(12) United States Patent
Andriolo et al.

(10) Patent No.: US 8,383,809 B2
(45) Date of Patent: Feb. 26, 2013

(54) PROCESS FOR THE PREPARATION OF DROSPIRENONE

(75) Inventors: Erika Andriolo, Milan (IT); Mauro Montorsi, Milan (IT); Stefano Rancan, Milan (IT); Edoardo Mariani, Milan (IT); Marco Bandini, Bologna (IT); Michele Contento, Bologna (IT); Achille Umani-Ronchi, Bologna (IT)

(73) Assignee: Newchem S.p.A., Milan (IT)

( * ) Notice: Subject to any disclaimer, the term of this patent is extended or adjusted under 35 U.S.C. 154(b) by 327 days.

(21) Appl. No.: 12/670,065

(22) PCT Filed: Jul. 21, 2008

(86) PCT No.: PCT/EP2008/005949
§ 371 (c)(1),
(2), (4) Date: Feb. 25, 2010

(87) PCT Pub. No.: WO2009/012955
PCT Pub. Date: Jan. 29, 2009

(65) Prior Publication Data
US 2010/0222571 A1    Sep. 2, 2010

(30) Foreign Application Priority Data

Jul. 26, 2007 (EP) .................................. 07014742

(51) Int. Cl.
*C07J 53/00* (2006.01)
(52) U.S. Cl. ......................... 540/15; 552/513
(58) Field of Classification Search ............ 540/15; 552/513
See application file for complete search history.

(56) References Cited

FOREIGN PATENT DOCUMENTS

| EP | 0 051 143 | 5/1982 |
| EP | 1 571 153 | 9/2005 |
| WO | 2006/059167 | 6/2006 |
| WO | 2006/061309 | 6/2006 |

OTHER PUBLICATIONS

Bittler, D. et al., "Synthesis of a newly highly effective aldosterone antagonist (spirorenone)" Angewandte Chemie, 94 (9), 718-719, 1982.

*Primary Examiner* — Brenda Coleman
(74) *Attorney, Agent, or Firm* — Lucas & Mercanti, LLP

(57) ABSTRACT

A process for the preparation of Drospirenone (I) according to the scheme (A) wherein the substituent R is defined in the description. The process improves the product yield and purity by reducing the formation of undesired side-products and is particularly convenient for industrial-scale manufacturing.

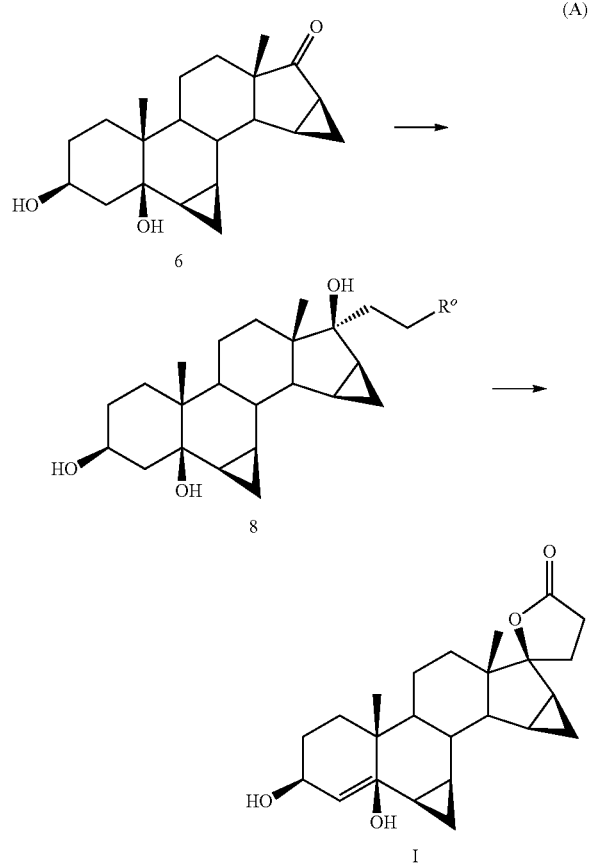

14 Claims, No Drawings

PROCESS FOR THE PREPARATION OF DROSPIRENONE

This application is a 35 U.S.C. §371 national phase of PCT/EP2008/005949 filed on Jul. 21, 2008, which claims priority to and the benefit of European Application No. 07014742.6 filed on Jul. 26, 2007, the contents of which are incorporated herein by reference.

The invention relates to a new process for the preparation of drospirenone and to synthetic intermediates thereof. Compared to known drospirenone synthetic routes, the process of the invention allows increased product yields, high purity and can be performed on an industrial scale.

STATE OF THE ART

Drospirenone is a synthetic progestin widely used in contraceptive therapy. Chemically known as 6β,7β,15β,16β-dimethylen-3-oxo-17α-pregn-4-ene-21,17-carbolactone, it has the following structural formula I

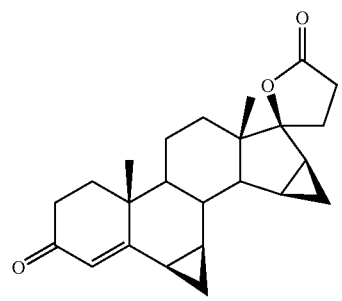

I

Several synthetic routes for the production of drospirenone have been proposed so far, for instance U.S. Pat. No. 6,121,465, WO2006/059168, WO2006/061309, US2005/0192450, WO2007/009821, U.S. Pat. Nos. 6,933,395, 4,416,985. A synthetic pathway common to many processes starts from 7β-hydroxy-15β,16β-methylen-3β-pivaloyloxy-5-androsten-17-one 1, which is transformed into 3β,5-dihydroxy-6β,7β,15β,16β-dimethylen-5β-androst-17-one 6 through the following steps:

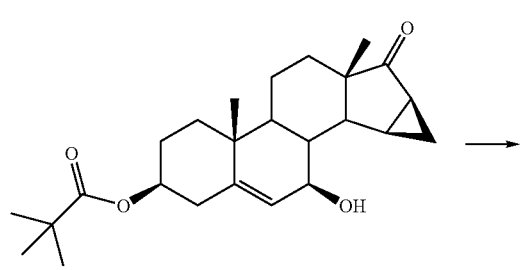

1

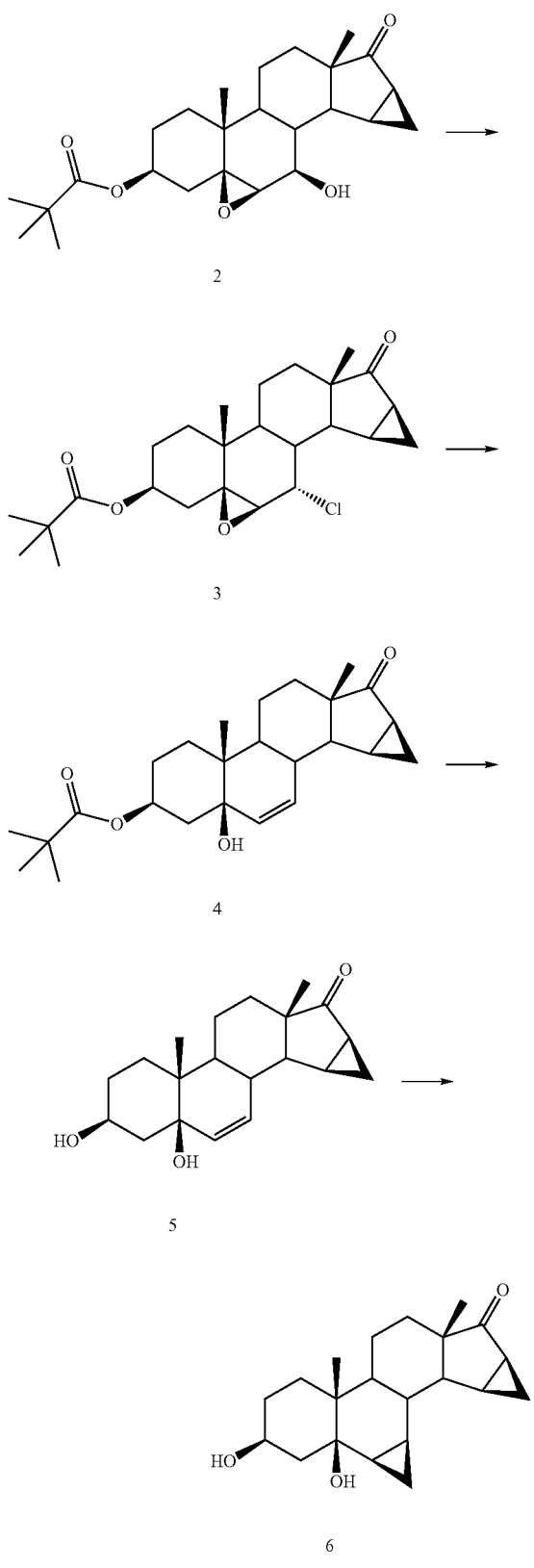

Intermediate 6 is then converted into the propynol-derivative 7 by reaction with propargyl alcohol

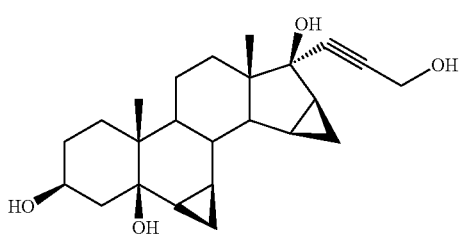

7

The triple bond at the 17α carbon chain is hydrogenated and the (3-hydroxypropyl) thus obtained derivative is suitably oxidized with simultaneous oxidative lactonization in position 17, dehydration in positions 4-5 and carbonyl formation at carbon 3, to give drospirenone (I). Different oxidizing agents may be used in the final step, such as chromium (VI) oxide in water/pyridine at 50° C. (U.S. Pat. No. 4,416,985), manganese dioxide in toluene at a temperature between 40° C. and 110° C. (US2005/0192450), ruthenium salts with $NaBrO_3$ in acetonitrile-water mixture (U.S. Pat. No. 6,121,465) or alkali hypochlorite (WO2007/009821). In all cases, the reduction of the propynol group in position 17 and the subsequent oxidative lactonization may affect the process yield and cause undesired epimerizations.

DESCRIPTION OF THE INVENTION

The invention provides a process for the production of drospirenone which improves the product yield and purity by reducing the formation of undesired side-products, such as epimers, and which is particularly convenient for industrial-scale manufacturing, according to the following steps:

1) reaction of compound of formula 6

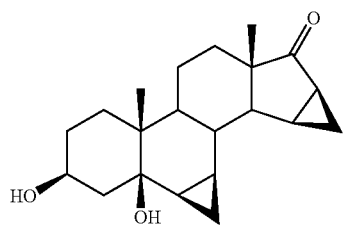

6 with a compound of formula II:

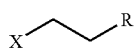

II wherein X is halogen and R— is selected from:

a) —$CH_2$—$OR^I$, wherein $R^I$ is a hydroxyl-protecting group which is preferably:

i) a silyl derivative $Q_3Si$—, wherein Q, independently from one another, represents ($C_1$-$C_6$)alkyl, ($C_6$-$C_{10}$)aryl, ($C_1$-$C_4$)alkylaryl or ($C_1$-$C_4$)alkoxyaryl, ii)

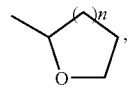

wherein n is 1 or 2;

b)

wherein $R^{II}$ and $R^{III}$, independently from one another, are ($C_1$-$C_3$)alkyl or $R^{II}$ and $R^{III}$, together with the oxygen atoms they are attached to, form a 1,3-dioxane or 1,3-dioxolane;

whereby a compound of formula 8 is obtained:

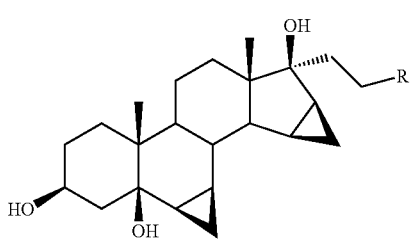

8

2) oxidation of a compound of formula 8 with removal of protecting groups $R^I$, $R^{II}$ or $R^{III}$ to give drospirenone I:

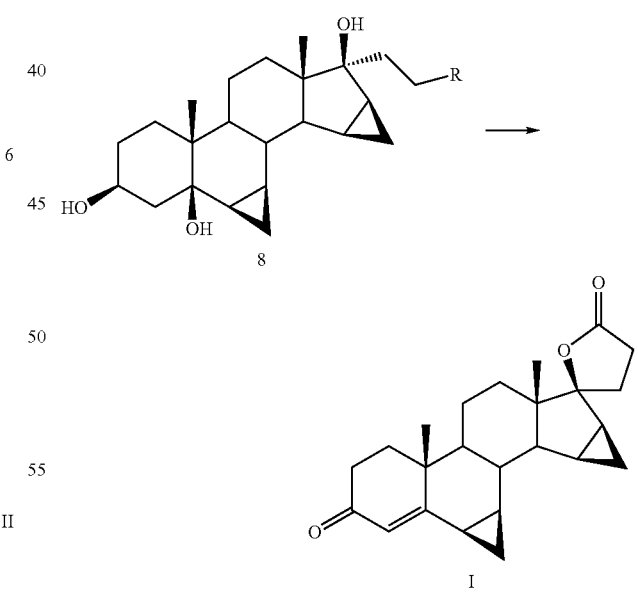

In a preferred embodiment of the invention, in compound II R is —$CH_2$—$OR^I$, wherein $R^I$ is selected from the group consisting of trimethylsilyl-, tert-butyldimethylsilyl-, triethylsilyl-, triisopropylsilyl-, dimethylisopropylsilyl-, diethylisopropylsilyl-, dimethyl(2,3-dimethylbutyl)silyl-, tert-butyldiphenylsilyl-, tribenzylsilyl-, tri-p-xylylsilyl-, diphenylmethylsilyl-, di-tert-butylmethylsilyl-, dimethylphenylsilyl-, 3,5-bis(trifluoromethyl)phenyldimethylsilyl-, tert-butylmethoxyphenylsilyl-, tert-butoxydiphenylsilyl-, (chloromethyl)dimethylsilyl-, allyldimethylsilyl-, triphenylsilyl-.

In a further preferred embodiment, the reaction step 1 is carried out in an aprotic solvent in the presence of lithium. Alternatively, compound II is transformed into the corresponding alkyl-magnesium derivative prior to its reaction with compound 6.

The oxidation according to step 2 may be carried out using a $Cr^{VI}$ or $Mn^{IV/VII}$-based oxidant, in a single step or by two or three steps, with or without isolation of the intermediate(s), depending on the specific oxidizing agent employed and on the reaction conditions adopted. Preferably, the $Cr^{VI}$ or $Mn^{IV/VII}$-based oxidant is selected from:

i) $CrO_3$ (Jones reagent);
ii) Pyridinium-dichromate;
iii) $MnO_2$;
iv) $KMnO_4$;

In one embodiment, compound 8 is oxidized, and any protecting group removed therefrom, in a one-step reaction by means of Jones reagent. Alternatively, the oxidation is performed first by reaction with o-iodoxybenzoic acid (IBX) and then the conversion to drospirenone is completed with Jones reagent.

In another embodiment, the oxidation step is carried out by first oxidising compound 8 at the "A" ring with manganese dioxide, with simultaneous loss of water to afford intermediate 9

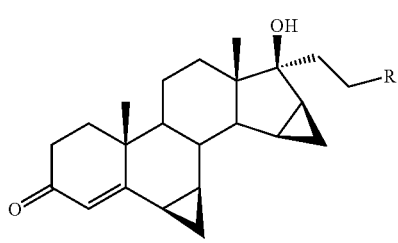

which is then deprotected and oxidized to lactone with Jones reagent. Such a two-step oxidation allows to reduce the amount of chromium (VI) necessary to obtain drospirenone.

In another embodiment, compound 8 with R=—CH$_2$—OR$^I$ wherein R' is alkyl(aryl)silyl, is first oxidized at the "A" ring with manganese dioxide, to yield intermediate 9, which is then hydrolized to remove the R$^I$ group, thus yielding intermediate 10:

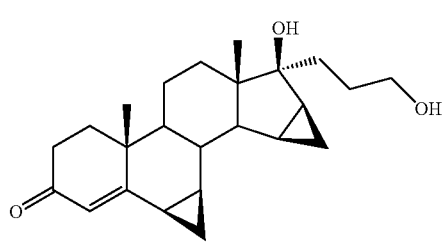

which can be isolated and then oxidized to lactone with manganese dioxide, to produce drospirenone.

In a yet further embodiment, compound 8 with R=—CH$_2$—OR$^I$ wherein R$^I$ is alkyl(aryl)silyl is hydrolysed to give intermediate 11:

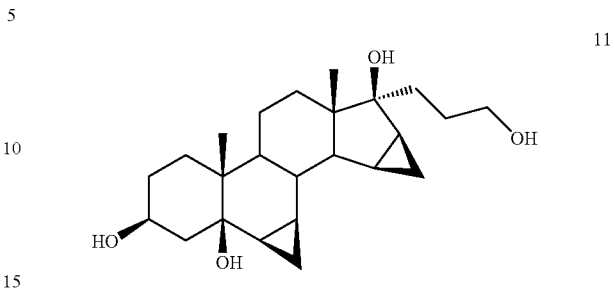

which can be purified by crystallisation and then oxidised with manganese dioxide to produce drospirenone. This alternative oxidation process allows to completely avoid the use of chromium.

Particularly preferred are the following conditions applicable to the oxidation step:

i) $CrO_3$ (Jones reagent) in water/acetone mixture at a temperature ranging from −20° C. to 10° C. or in 1,2-dimethoxyethane/water at a temperature ranging from −20° C. to 30° C. or in N,N-dimethylformamide/water at a temperature ranging from −20° C. to 30° C.;

ii) IBX in DMSO at 20° C. followed by $CrO_3$ (Jones reagent) in water/acetone mixture at a temperature ranging from −20 to 10° C.;

iii) Pyridinium-dichromate in DMF at a temperature ranging from 0° C. to 50° C.;

iv) $MnO_2$ in toluene or in one or more of the following solvents: tetrahydrofuran, acetonitrile, dimethylsufoxide, N,N-dimethylformamide, acetone, at a temperature ranging from 40° C. to 110° C.;

v) $KMnO_4$ in water/acetone in the presence of a protic acid at a temperature ranging from −10° C. to 40° C.

At the end of the process, drospirenone can be directly purified by crystallization.

The starting compound 6 (3β,5-dihydroxy-6β,7β,15β,16β-dimethylen-5β-androstan-17-one) can be prepared with known methods—reference is specifically made to U.S. Pat. No. 4,416,985, Example 1 steps (a) to (f) and US2005/0192450, page 6 Example 4. In a preferred embodiment of the invention, compound 6 is prepared according to the following steps:

a) epoxydation of 7β-hydroxy-15β,16β-methylen-3β-pivaloyloxy-5-androsten-17-one (1) with tert-butylhydroperoxide in the presence of vanadyl acetylacetonate in toluene at 70-75° C., to give 5,6β-epoxy-7β-hydroxy-15β,16β-methylen-3β-pivaloyloxy-5β-androstan-17-one 2:

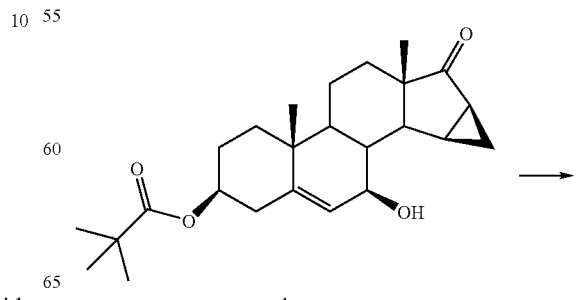

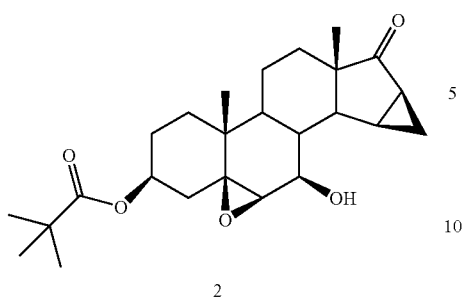

2

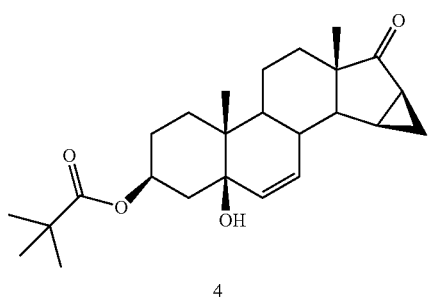

4 b) reaction of compound 2 with hexachloroacetone in dichloromethane added with triphenylphosphine at a temperature of 0-5° C. followed by heating to 10-15° C., to yield 7α-chloro-5,6β-epoxy-15β,16β-methylen-3β-pivaloyloxy-5β-androstan-17-one 3:

d) removal of the pivaloyl group at carbon 3 of compound 4 with potassium hydroxide in a tetrahydrofuran/methanol mixture in the presence of sodium perchlorate at room temperature, followed by addition of sulfuric acid up to pH 7, whereby 3β,5-dihydroxy-15β,16β-methylen-5β-androst-6-en-17-one 5 is obtained:

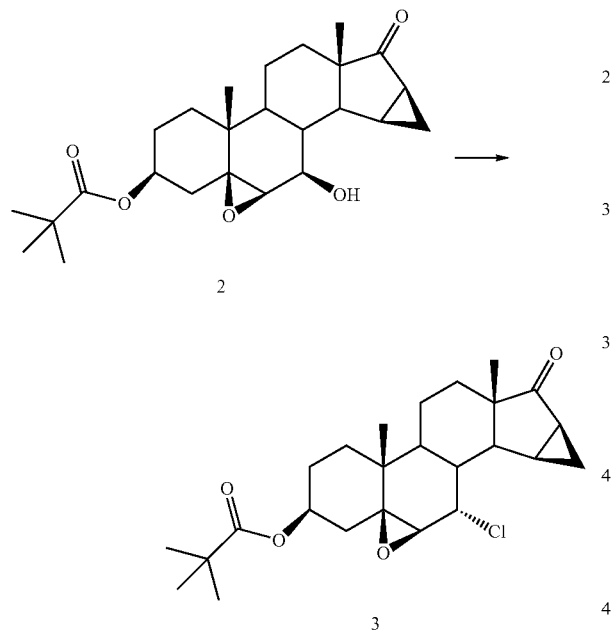

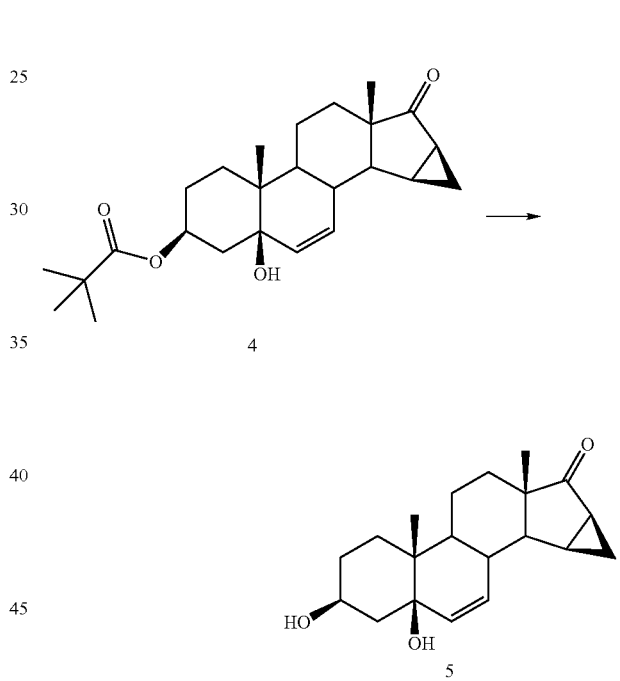

c) opening of the epoxy ring of compound 3 with simultaneous removal of the chlorine atom, by reaction with acetic acid, zinc and copper bromide in 1,2-dimethoxyethane heating up to 70° C., to obtain 5-hydroxy-15β,16β-methylen-3β-pivaloyloxy-5β-androst-6-en-17-one 4:

e) conversion of compound 5 into 3β,5-dihydroxy-6β,7β,15β,16β-dimethylen-5β-androst-17-one 6 by reaction with dibromomethane in 1,2-dimethoxyethane in the presence of zinc and copper bromide by heating up to 75° C., followed by addition of acetic acid and isopropanol:

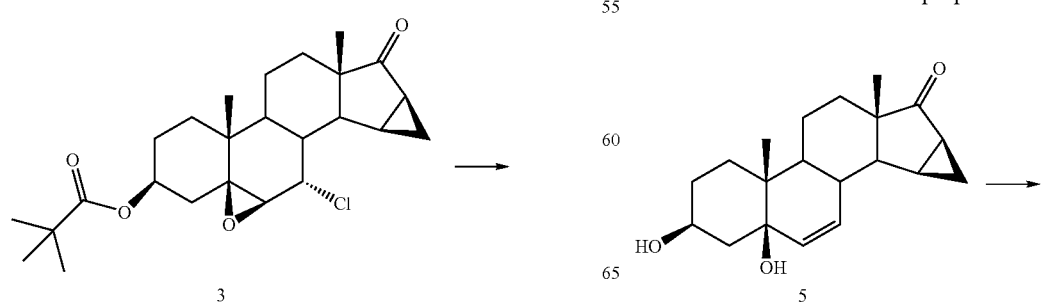

-continued

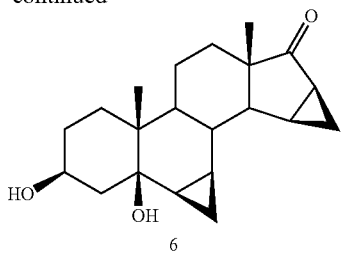
6

The starting compound 7β-hydroxy-15β,16β-methylen-3β-pivaloyloxy-5-androsten-17-one 1 is commercially available or it can be prepared as described in U.S. Pat. No. 4,416,985 (Example 4).

A further aspect of the invention relates to the following compounds:

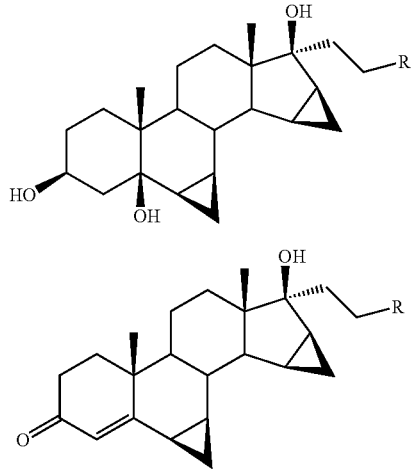

wherein R is as defined above, as intermediates for the synthesis of drospirenone.

Unlike known methods for preparing drospirenone, the process of the invention presents the advantage of avoiding any hydrogenation step, which usually produces not only 17α-[3-hydroxypropyl]-6β,7β,15β,16β-dimethylen-5β-androstan-3β,5,17β-triol, but also 6β,7β,15β,16β-dimethylen-5β-androstan-3β,5,17β-trihydroxy-21,17-carbolactol, together with partially hydrogenated side-products. Consequently the isolation of the desired products—the triol and the carbolactol—results quite troublesome and causes the loss of products.

Moreover the preparation of compound 8 according to the invention can be carried out without any specific equipment, which instead is required when hydrogenation is needed. Dispensing with the hydrogenation step makes the entire process more attractive on industrial scale.

A further important advantage associated with the invention is the fact that no purification by column chromatography is necessary to isolate the intermediates, especially in the case of silyl derivatives which can be directly oxidized to drospirenone without being isolated. In this case the crude drospirenone presents a HPLC purity level of 95-96% and consequently may necessitate only crystallisation (e.g. from acetone) to satisfy the pharmacopoeia requirements.

The following examples illustrate the invention in greater detail.

EXAMPLE 1

5,6β-Epoxy-7β-hydroxy-15β,16β-methylen-3β-pivaloyloxy-5β-androstan-17-one

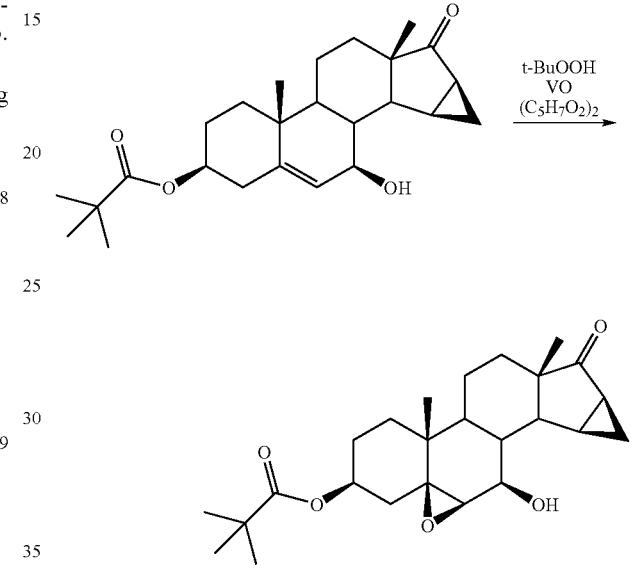

7β-hydroxy-15β,16β-methylen-3β-pivaloyloxy-5-androsten-17-one (200.00 g, 0.500 mol) is dissolved in toluene (1610 mL) at 70-75° C. under nitrogen atmosphere in the presence of vanadyl acetylacetonate (1.02 g, 0.004 mol).

A solution of tert-butylhydroperoxide (5.5 M in decane, 135 mL, 0.742 mol) in toluene (231 mL) is added dropwise. After two hours TLC analysis reveals that the reaction is complete and sodium chloride in water (6%, 700 mL) is added. The system is stirred for five minutes and the two phases are separated. The organic phase is washed twice with a solution of sodium chloride in water (6%, 2×600 mL). The aqueous phase is extracted with toluene (250 mL) and the combined organic phases are washed twice with sodium chloride in water (6%, 2×50 mL) and concentrated at 50° C. under reduced pressure to a final volume of about 300 mL. n-Hexane (760 mL) is then added and the product is filtered and washed with n-hexane. After drying at 45° C. in a vacuum oven the title compound is obtained as a colourless powder (187.7 g, 0.451 mol, 90%).

$^1$H-NMR {300 MHz, CDCl$_3$, δ (ppm)}: 0.93 (s, 3H, CH$_3$-18); 2.14-0.91 (17 H); 1.05 (s, 3H, CH$_3$-19); 1.17 (s, 9H, C(CH$_3$)$_3$); 2.32 (m, 1H, H-17); 3.25 (d, 1H, J=0.9 Hz, H-6); 3.75 (dd, 1H, J=8.7, 0.9 Hz, H-7); 4.74 (m, 1H, H-3).

$^{13}$C-NMR {300 MHz, CDCl$_3$, δ (ppm)}: 16.6 (CH$_3$); 17.3 (CH$_3$); 19.6 (CH$_3$); 20.6 (CH$_2$); 25.2 (CH); 26.5 (CH); 26.9 (CH$_2$); 27.0 (3×CH$_3$, C(CH$_3$)$_3$); 34.7 (C); 34.9 (CH$_2$); 36.3 (CH); 36.5 (CH$_2$); 37.4 (CH$_2$); 38.5 (C); 42.1 (C); 49.9 (CH); 50.7 (CH); 66.7 (C); 67.2 (CH); 70.2 (CH); 73.3 (CH); 177.9 (C); 216.1 (C)

HPLC-MS (ESI): [M+H]⁺=417; [M+Na]⁺=439; [M+K]⁺=455; [2M+Na]⁺=855

EXAMPLE 2

7α-Chloro-5,6β-epoxy-15β,16β-methylen-3β-pivaloyloxy-5β-androstan-17-one

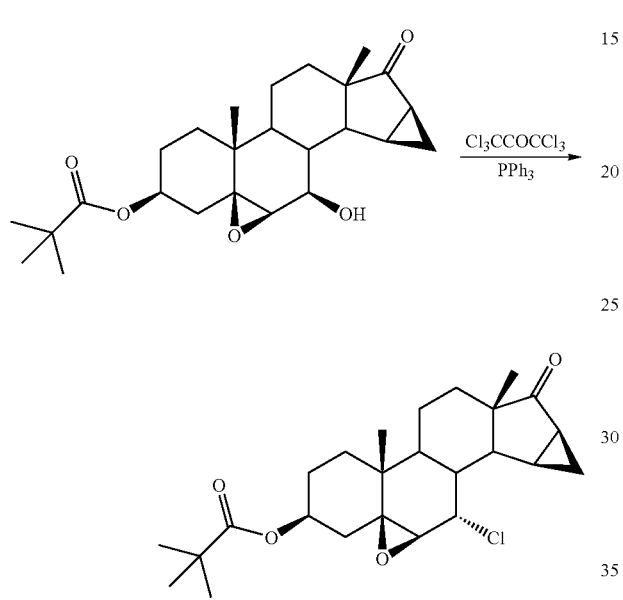

A solution of 5,6β-epoxy-7β-hydroxy-15β,16β-methylen-3β-pivaloyloxy-5β-androstan-17-one (1.66 g, 0.004 mol) in dichloromethane (8 mL) is treated with hexachloroacetone (2 mL, 0.013 mol) and cooled to 0-2° C. Triphenylphosphine (1.53 g, 0.0044 mol) in dichloromethane (4 mL) is added dropwise and the mixture is stirred for one hour at 3-4° C., then for an additional hour at 10-15° C.

The reaction mixture is diluted with dichloromethane (20 mL) and washed three times with water. The combined aqueous phases are extracted with dichloromethane and the organic layers are dried on sodium sulphate and concentrated at 45° C. under reduced pressure. The residue is suspended in ethanol (5 mL), stirred for 15 minutes and filtered. After drying at 40° C. under vacuum the title compound is obtained as a colourless solid (1.40 g, 0.003 mol, 80%).

$^1$H-NMR {300 MHz, CDCl₃, δ (ppm)}: 0.94 (s, 3H, CH₃-18); 2.17-1.12 (17H); 1.05 (s, 3H, CH₃-19); 1.17 (s, 9H, C(CH₃)₃); 3.36 (d, J=3 Hz, 1H, H-6); 4.68 (m, 1H, H-7); 4.79 (m, 1H, H-3).

$^{13}$C-NMR {300 MHz, CDCl₃, δ (ppm)}: 16.9 (CH₂); 17.4 (CH₃); 19.9 (CH); 20.5 (CH₂); 20.8 (CH₃); 25.6 (CH₂); 26.7 (CH); 27.0 (3×CH₃, C(CH₃)₃); 31.9 (CH); 35.0 (C); 35.3 (C); 35.9 (CH₂); 37.3 (CH₂); 38.5 (CH₂); 42.0 (CH); 43.5 (C); 48.5 (CH); 55.0 (CH); 64.1 (C); 65.1 (CH); 70.5 (CH); 177.8 (C); 215.1 (C).

HPLC-MS (ESI): [M+H]⁺=435 and 437; [2M+Na]⁺=891 and 893

EXAMPLE 3

5-Hydroxy-15β,16β-methylen-3β-pivaloyloxy-5β-androst-6-en-17-one

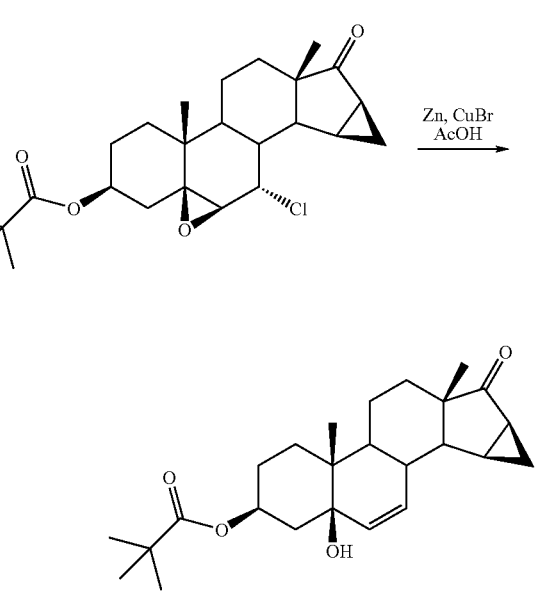

A suspension of zinc powder (2.95 g, 0.045 mol) in 1,2-dimethoxyethane (37 mL) is treated with copper (I) bromide (0.07 g, 0.0005 mol) and heated up to 70° C. After stirring for 15 minutes acetic acid (1.11 mL, 0.019 mol) is added followed by 7α-chloro-5,6β-epoxy-15β,16β-methylene-3β-pivaloyloxy-5β-androstan-17-one (1.30 g, 0.003 mol). The mixture is stirred at 70° C. for 6 hours and then at room temperature for 16 hours. The reaction is checked by TLC analysis; the mixture is filtered on a celite pad washing with tetrahydrofuran (37 mL). The filtrate is treated with triethylamine (1.66 mL) and filtered again. The solid is suspended in 5% acetic acid solution (37 mL) and then filtered (1.11 g).

The product is crystallized from ethyl acetate/dichloromethane (0.92 g, 0.002 mol, 77%)

$^1$H-NMR {200 MHz, CDCl₃, δ (ppm)}: 0.99 (s, 3H, CH₃-18); 1.01 (s, 3H, CH₃-19); 1.1-2.4 (17H) 1.24 (s, 9H, C(CH₃)₃); 2.84 (s, 1H, OH-5); 5.16 (bs, 1H, H-3); 5.58 (dd, J=2.6, 10.2 Hz, 1H, H-7); 5.75 (dd, J=1.2, 10.2 Hz, 1H, H-6).

$^{13}$C-NMR {200 MHz, CDCl₃, δ (ppm)}: 17.6 (CH₂); 18.3 (CH₃); 20.4 (CH₃); 20.5 (CH₂); 22.1 (CH); 24.7 (CH₂) 25.5 (CH₂); 26.0 (CH); 27.3 (3×CH₃); 35.3 (CH₂); 35.7 (CH); 39.4 (C); 39.5 (CH₂); 43.0 (C); 44.8 (CH); 50.8 (CH); 70.3 (CH); 74.3 (C); 126.6 (CH); 135.4 (CH); 177.0 (C); 198.1 (C); 215.9 (C).

HPLC-MS (ESI): [M+Na]⁺=423; [M+K]⁺=439

EXAMPLE 4

3β,5-Dihydroxy-15β,16β-methylen-5β-androst-6-en-17-one

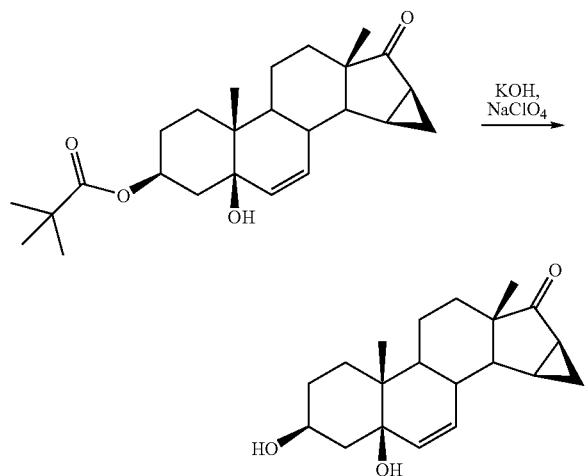

5-Hydroxy-15β,16β-methylene-3β-pivaloyloxy-5β-androst-6-en-17-one (80.00 g, 0.200 mol) is suspended under nitrogen in tetrahydrofuran (800 mL), mechanically stirred and cooled to 0-2° C. A solution of potassium hydroxide (85%, 27.69 g, 0.419 mol) in methanol (410 mL) is added dropwise below 5° C. followed by sodium perchlorate monohydrate (7.85 g, 0.056 mol). The mixture is stirred at room temperature for 3-4 hours. After cooling to 4-5° C., water (400 mL) is added followed by 20% sulfuric acid in water (90 mL) adjusting the pH to 7 and the mixture is stirred for 10-15 minutes. Tetrahydrofuran and methanol are then removed at 40° C. under reduced pressure and the residue is diluted with water (300 mL). The suspension is stirred at 5° C. for 30 minutes and the solid is filtered, washed with water and dried at 45° C. in a vacuum oven for 16 hours. The title compound is obtained as a colourless solid (61.00 g, 0.192 mol, 97%) and is used in the next step without purification.

$^1$H-NMR {200 MHz, CDCl$_3$, δ (ppm)}: 0.995 (s,3H, CH$_3$-18); 1.02 (s, 3H, CH$_3$-19); 1.1-2.3 (17H); 2.85 (m, 1H, OH); 3.04 (m, 1H, OH); 4.13 (m, 1H, H-3); 5.58 (dd, J=2.8, 10 Hz, 1H, H-7); 5.73 (dd, J=1.6, 10 Hz, 1H, H-6).

$^{13}$C-NMR {200 MHz, CDCl$_3$, δ (ppm)}: 17.5 (CH$_2$); 18.0 (CH$_3$); 20.2 (CH$_3$); 20.3 (CH$_2$); 22.0 (CH); 24.5 (CH$_2$); 25.7 (CH); 27.7 (CH$_2$); 35.1 (CH$_2$); 35.5 (CH); 39.1 (C) 40.6 (CH$_2$); 42.8 (C); 44.6 (CH); 50.5 (CH); 66.9 (CH); 75.5 (C); 126.0 (CH); 135.4 (CH); 216.2 (C).

HPLC-MS (ESI): [M+H]$^+$=317; [M+Na]$^+$=439; [M+K]$^+$=355 [2M+Na]$^+$=655

EXAMPLE 5

3β,5-Dihydroxy-6β,7β,15β,16β-dimethylen-5β-androst-17-one

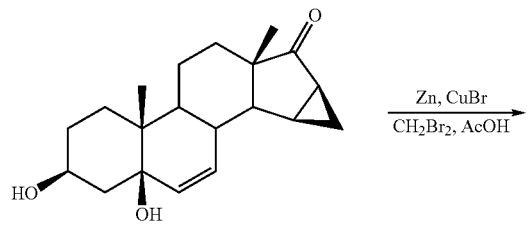

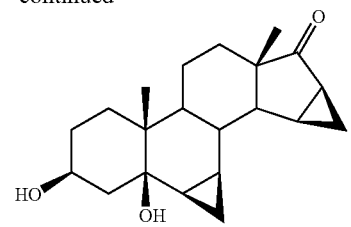

Zinc (powder, 135.00 g, 2.065 mol) and copper (I) bromide (5.00 g, 0.035 mol) are suspended in 1,2-dimethoxyethane (1820 mL) under nitrogen atmosphere; the mixture is heated up to 75° C. and stirred for 20 minutes. 3β,5-dihydroxy-15β,16β-methylen-5β-androst-6-en-17-one (100.00 g, 0.316 mol) is added and the mixture is stirred for 15 minutes. The system is then treated with acetic acid (4.5 mL, 0.078 mol) and isopropanol (9.5 mL, 0.124 mol) and stirred at 72° C. A solution of dibromomethane (334 g, 1.921 mol) in 1,2-dimethoxyethane (114 mL) is added dropwise at such a rate that the temperature is maintained around 75° C. The mixture is stirred for one hour until TLC analysis reveals that the conversion of the starting material is complete.

Ethyl acetate (2500 mL) is added and the system is cooled to 0-5° C. After 5% acetic acid in water (2500 L) is slowly added, stirring is maintained for 30 minutes. The solid is filtered and the liquid phases are separated. The aqueous layer is extracted twice with ethyl acetate (1250 mL, 500 mL) and the combined organic phases are washed twice with water (2×2500 mL) and separated. After removing the organic solvent at 45° C. under reduced pressure the residue is taken up in diisopropyl ether (560 mL), stirred, filtered and washed twice with diisopropyl ether. The title compound is dried at 45° C. in vacuo (74.50 g, 0.225 mol, 71%).

$^1$H-NMR {200 MHz, CDCl$_3$, δ (ppm)}: 0.86 (s, 3H, CH$_3$-18); 0.6-2.3 (21H); 0.95 (s, 3H, CH$_3$-19); 3.00 (bs, 2H, 2(OH)); 4.06 (m, 1H, H-3).

$^{13}$C-NMR {200 MHz, CDCl$_3$, δ (ppm)}: 11.7 (CH$_2$); 13.9 (CH); 17.6 (CH$_2$); 19.0 (CH$_3$); 20.1 (CH$_3$); 21.1 (CH$_2$); 22.3 (CH); 25.0 (CH); 25.9 (CH); 26.7 (CH$_2$); 27.6 (CH$_2$); 33.3 (CH); 34.9 (CH$_2$); 40.5 (C); 43.0 (C); 42.9 (CH$_2$); 45.4 (CH); 51.9 (CH); 66.9 (CH); 74.5 (C); 216.3 (C).

HPLC-MS (ESI): [M+Na]$^+$=353; [2M+Na]$^+$=683

EXAMPLE 6

(3-Chloropropoxy)trimethylsilane

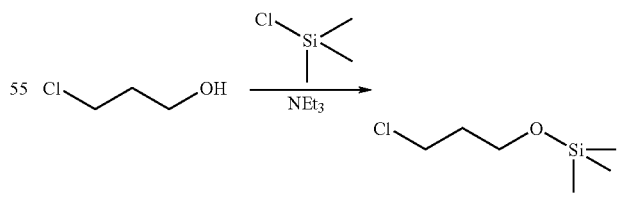

3-Chloropropanol (100.00 g, 1.056 mol) is mechanically stirred in dichloromethane (1200 mL) under nitrogen atmosphere; after cooling the solution to 0° C., triethylamine (176 mL, 1.263 mol) is added.

A solution of chlorotrimethylsilane (126.40 g, 1.164 mol) in dichloromethane (300 L) is then added dropwise maintaining the temperature between 0° C. and 5° C. When the con-

EXAMPLE 7

17α-[3-(Trimethylsilanyloxy)propyl]-6β,7β,15β, 16β-dimethylen-5β-androstane-3β,5,17β-triol

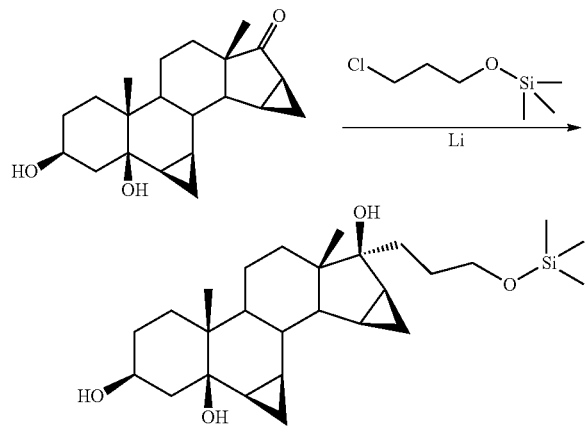

3β,5-Dihydroxy-6β,7β,15β,16β-dimethylen-5β-androst-17-one (65.00 g, 0.197 mol) is dissolved in tetrahydrofuran (975 mL) and cooled to −20° C. under nitrogen atmosphere. Lithium (granular, 13.65 g, 1.967 mol) is then added and stirred for 20 to 30 minutes. (3-Chloropropoxy)trimethylsilane (131.17 g, 0.787 mol) is added dropwise maintaining the temperature below −15° C. and the stirring is continued at a temperature between −20 and −15° C. The reaction is monitored by TLC analysis and when no more starting material is present (2.5 hours), the mixture is poured into water/ice/sodium bicarbonate (910 mL/1170 g/150 g) and vigorously stirred until the remaining lithium is completely dissolved. The mixture is extracted twice with ethyl acetate (1300 mL, 650 mL) and the organic layers are washed with water (325 mL, 160 mL). Removal of ethyl acetate under reduced pressure affords the crude product (127.1 g, quantitative yield) which is used in the subsequent step without further purification.

A sample of crude product is further purified by first decanting, then triturating and filtering from dichloromethane/n-hexane.

$^1$H-NMR {300 MHz, CDCl$_3$, δ (ppm)}: 0.21-2.80 (25H); 0.84 (s, 3H, CH$_3$-18); 088 (s, 3H, CH$_3$-19); 3.57-3.75 (m, 6H, 3×OH, CH$_2$—OSi).

$^{13}$C-NMR {300 MHz, DMSO-d$_6$, δ (ppm)}: −0.65 (3×CH$_3$); 7.7 (CH$_2$); 14.9 (CH); 15.9 (CH); 19.0 (CH$_3$); 19.1 (CH$_3$); 21.7 (CH$_2$); 22.7 (CH); 25.4 (CH$_2$); 27.0 (CH$_2$); 27.5 (CH$_2$); 33.5 (CH$_2$); 34.1 (CH); 36.5 (CH$_2$); 40.3 (C); 42.6 (CH$_2$); 43.0 (C); 44.9 (CH); 52.8 (CH); 63.3 (CH$_2$); 66.8 (CH); 67.7 (CH$_2$); 74.5 (C); 81.7 (C).

HPLC-MS (ESI): [M+Na]$^+$=485; [2M+Na]$^+$=947 version is complete, diisopropyl ether (600 mL) is added and triethylamine hydrochloride is filtered washing the pad with diisopropyl ether. The filtrate is concentrated at 38° C. under reduced pressure and the product is purified by distillation (0-5 mmHg, 70° C.). (3-Chloropropoxy)trimethylsilane is obtained as a colourless liquid (144.57 g, 0.867 mol, 82%).

$^1$H-NMR {300 MHz, CDCl$_3$, δ (ppm)}: 0.13 (s, 9H, CH$_3$); 1.96 (m, 2H, CH$_2$); 3.65 (t, J=6.3 Hz, 2H, Cl—CH$_2$); 3.72 (t, J=5.7 Hz, 2H, O—CH$_2$).

EXAMPLE 8 tert-Butyl-(3-chloropropoxy)dimethylsilane

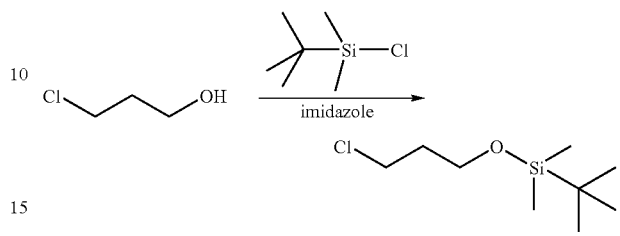

A solution of 3-chloropropanol (84.6 g, 0.895 mol) in dichloromethane (1600 mL) is treated with imidazole (121.9 g, 1.791 mol) under nitrogen atmosphere and cooled to 0-5° C.

tert-Butylchlorodimethylsilane (100.00 g, 0.663 mol) diluted with dichloromethane (160 mL) is added dropwise at 0-5° C.

After 2.5 hours the reaction is quenched by pouring the mixture into ice/water (423 g/1270 mL) and stirring for five minutes. The mixture is then allowed to reach 20° C. and the two layers are separated.

The aqueous phase is extracted with dichloromethane (850 mL) and the combined organic layers are washed with water (600 mL). The organic phase is concentrated at 40° C. under reduced pressure affording the product as a pale yellow oil (159.33 g, 0.763 mol, 85%) which is subsequently used without further purification.

$^1$H-NMR {300 MHz, CDCl$_3$, δ (ppm)}: 0.05 (s, 6H, Si—(CH$_3$)$_2$); 0.87 (s, 9H, Si—C(CH$_3$)$_3$); 2.01 (m, 2H, CH$_2$); 3.75 (t, J=6.3 Hz, 2H, Cl—CH$_2$); 3.82 (t, J=5.7 Hz, 2H, O—CH$_2$).

EXAMPLE 9

17α-[3-(tert-Butyldimethylsilanyloxy)propyl]-6β,7β, 15β,16β-dimethylen-5β-androstane-3β,5,17β-triol

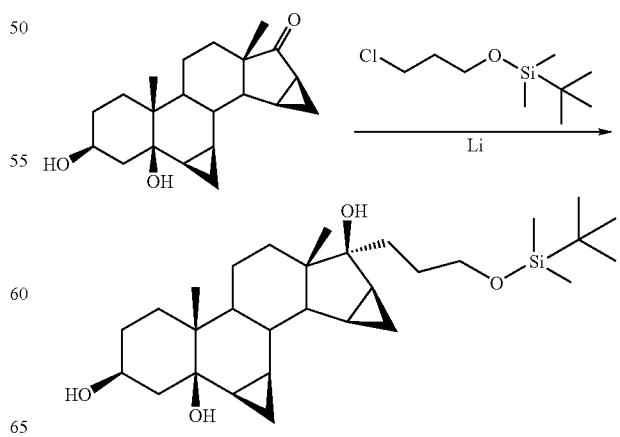

The compound is prepared as described in EXAMPLE 7 starting from 25.00 g (0.075 mol) of 3β,5-dihydroxy-6β,7β,15β,16β-dimethylen-5β-androst-17-one which is treated with lithium (6.03 g, 0.865 mol) and tert-butyl-(3-chloropropoxy)dimethylsilane (90.74 g, 0.434 mol).

An oily product is obtained (60.10 g, quantitative yield) and used in the subsequent step without further purification.

A sample of the compound is purified by column chromatography on silica gel, eluting with n-hexane/ethyl acetate, and isolated for the analytical characterization.

$^1$H-NMR {300 MHz, DMSO-d$_6$, δ (ppm)}: 0.1-2.1 (25H); 0.03 (s, 6H, Si—(CH$_3$)$_2$); 0.76 (s, 6H, CH$_3$-18 and CH$_3$-19); 0.87 (s, 9H, C(CH$_3$)$_3$); 3.6 (m, 3H, OH and CH$_2$-22); 3.84 (m, 1H, H-3); 4.35 (bs, 1H, OH); 4.84 (d, J=4.2 Hz, 1H, OH-3).

$^{13}$C-NMR {200 MHz, CDCl$_3$, δ (ppm)}: −5.2 (CH$_3$); −5.3 (CH$_3$); 7.9 (CH$_2$); 11.3 (CH); 14.5 (CH); 15.7 (CH); 18.0 (C); 18.9 (CH$_3$); 19.3 (CH); 19.4 (CH$_3$); 22.0 (CH$_2$); 22.6 (CH); 25.2 (CH$_2$); 25.8 (3×CH$_3$); 27.3 (CH$_2$); 27.8 (CH$_2$); 33.2 (CH$_2$); 34.2 (CH); 36.6 (CH$_2$); 40.0 (C); 42.4 (C); 43.6 (CH$_2$); 52.9 (CH); 63.7 (CH$_2$); 65.9 (CH); 67.0 (CH$_2$); 72.7 (C); 80.6 (C).

HPLC-MS (ESI): [M+Na]$^+$=527; [2M+Na]$^+$=1031

EXAMPLE 10

2-(3-Chloropropoxy)tetrahydropyran

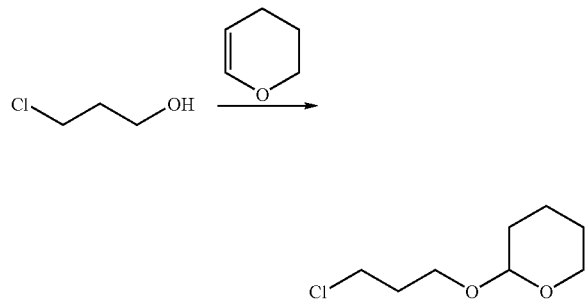

To a solution of 3-chloropropanol (20.00 g, 0.212 mol) in dichloromethane (100 mL) 3,4-dihydro-2H-pyran (16.02 g, 0.190 mol) diluted in dichloromethane (17 mL) is added dropwise at 0-5° C. The mixture is stirred for 30 minutes and the reaction (checked by TLC analysis) is quenched by washing with saturated sodium bicarbonate (100 mL). After separation the organic layer is washed with water (50 mL), dried over sodium sulfate, filtered and concentrated under reduced pressure at 30° C. (34.32 g).

The title compound is isolated by column chromatography on silica gel eluting with n-hexane:ethyl acetate) (31.28 g, 0.175 mol, 91%).

$^1$H-NMR {300 MHz, CDCl$_3$, δ (ppm)}: 1.2-2.0 (6H); 2.09 (m, 2H, CH$_2$); 3.56 (m, 2H, Cl—CH$_2$); 3.70 (m, 2H, O—CH$_2$); 3.92 (m, 2H, O—CH$_2$); 4.65 (m, 1H, O—CH—O).

GC-MS (EI): [M−H]$^+$=177; [M−ClCH$_2$CH$_2$CH$_2$O]$^+$=85

EXAMPLE 11

17α-[3-(Tetrahydropyran-2-yloxy)propyl]-6β,7β,15β,16β-dimethylen-5β-androstane-3β,5,17β-triol 3β,5-Dihydroxy-6β,7β,15β,16β-dimethylen-5β-androst-17-one (8.00 g, 0.024 mol) is dissolved in tetrahydrofuran (117 mL) and cooled to −20° C. under nitrogen atmosphere. Lithium (granular, 1.68 g, 0.242 mol) is then added and stirred for 20 minutes. 2-(3-Chloropropoxy)tetrahydropyran (21.62 g, 0.121 mol) is added dropwise maintaining the temperature below −15° C. and stirring is continued at a temperature between −20 and −15° C. The reaction is monitored by TLC analysis and when no more starting material is present (2.5 hours), the mixture is poured into water/ice/sodium bicarbonate (112 mL/16 g/144 g) and vigorously stirred until the remaining lithium is completely dissolved. The mixture is extracted twice with ethyl acetate (160 mL, 80 mL) and the organic layers are washed with water (2×40 mL). After separation, removal of ethyl acetate at 50° C. under reduced pressure affords 22.50 g of crude product which is purified by column chromatography on silica gel eluting with n-hexane/ethyl acetate and obtained as a colourless powder (11.41 g, 99%).

$^1$H-NMR {300 MHz, DMSO-d$_6$, δ (ppm)}: 0.17 (m, 1H, cyclopropyl); 0.47 (m, 1H, cyclopropyl); 0.64-2.11 (29 H); 0.78 (s, 6H, CH$_3$-18 and CH$_3$-19); 3.26-3.85 (m, 5H); 4.16 (s, 1H, OH); 4.35 (bs, 1H, OH); 4.55 (m, 1H, O—CH—O); 4.84 (d, 1H, OH-3).

$^{13}$C-NMR {300 MHz, CDCl$_3$, δ (ppm)}: 7.7 (CH$_2$); 11.6 (CH$_2$); 15.0 (CH); 16.0 (CH); 19.0 (CH$_3$); 19.1 (CH$_3$); 19.5 (CH$_2$); 21.7 (CH$_2$); 22.7 (CH); 24.1 (CH$_2$); 25.0 (CH); 25.3 (CH$_2$); 26.7 (CH$_2$); 27.5 (CH$_2$); 30.5 (CH$_2$); 33.7 (CH$_2$); 34.2 (CH); 36.5 (CH$_2$); 40.3 (C); 42.6 (C); 43.0 (CH$_2$); 44.9 (CH); 52.9 (CH); 62.3 (CH$_2$); 66.9 (CH); 68.2 (CH$_2$); 74.6 (C); 81.9 (C); 98.7 (CH).

HPLC-MS (ESI): [M+Na]$^+$=497.

EXAMPLE 12

17α-(2-[1,3]Dioxolan-2-ylethyl)-6β,7β,15β,16β-dimethylen-5β-androstane-3β,5,17β-trial

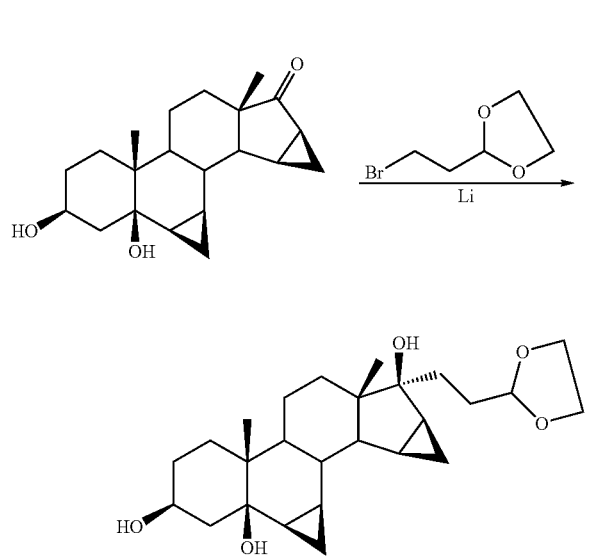

3β,5-dihydroxy-6β,7β,15β,16β-dimethylen-5β-androst-17-one (60.00 g, 0.182 mol) is dissolved in tetrahydrofuran (900 mL) and cooled to −20° C. Lithium (granular, 13.86 g, 2.003 mol) is then added and stirred for 20 to 30 minutes. 2-(2-Bromoethyl)-1,3-dioxolane (180.81 g, 0.999 mol) is added dropwise maintaining the temperature below 0° C. and stirring is continued between −20 and −15° C. The reaction is monitored by TLC analysis and when no more starting material is present (2 hours), the mixture is poured into water/ice/sodium bicarbonate (830 mL/1070 g/120 g) and vigorously stirred until the remaining lithium is completely dissolved. The mixture is extracted twice with ethyl acetate (1100 mL, 850 mL) and the organic layers are washed with water (800 mL, 700 mL). After separation of the phases, removal of ethyl acetate at 50° C. under reduced pressure affords the crude product as an oily mixture (110.44 g).

Purification performed by column chromatography on silica gel eluting with n-hexane/ethyl acetate affords the title compound (64.25 g, 0.149 mol, 82%).

$^1$H-NMR {200 MHz, CDCl$_3$, δ (ppm)}: 0.34-2.28 (26H); 0.86 (s, 3H, CH$_3$-18); 0.90 (s, 3H, CH$_3$-19); 2.54 (s, 1H, OH-17); 3.34 (d, J=6 Hz, 1H, OH-3); 4.05-3.85 (m, 5 H, H-3, 2×CH$_2$—O); 4.95 (t, J=4.6 HZ, 1H, O—CH—O).

$^{13}$C-NMR {200 MHz, CDCl$_3$, δ (ppm)}: 7.8 (CH$_2$); 11.6 (CH$_2$); 15.0 (CH); 16.0 (CH); 19.0 (CH$_3$); 19.2 (CH$_3$); 21.7 (CH$_2$); 22.5 (CH); 25.0 (CH); 26.7 (CH$_2$); 27.6 (CH$_2$); 28.2 (CH$_2$); 30.8 (CH$_2$); 34.2 (CH); 36.5 (CH$_2$); 40.3 (C); 42.7 (C); 43.0 (CH$_2$); 44.8 (CH); 52.7 (CH); 64.8 (2×CH$_2$); 67.0 (CH); 74.7 (C); 81.8 (C); 105.0 (CH).

HPLC-MS (ESI): [M+Na]$^+$=455; [M+K]$^+$=471; [2M+Na]$^+$=887

EXAMPLE 13

17α-(2-[1,3]Dioxan-2-ylethyl)-6β,7β,15β,16β-dimethylen-5β-androstane-3β,5,17β-triol

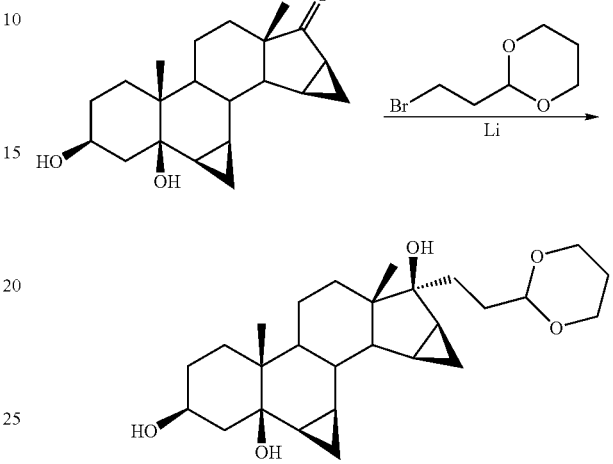

The title compound is prepared as described in EXAMPLE 12 by reaction of 3β,5-dihydroxy-6β,7β,15β,16β-dimethylen-5β-androst-17-one (30.00 g, 0.091 mol) with 2-(2-bromoethyl)-1,3-dioxane (97.20 g, 0.498 mol) in the presence of lithium (granular, 7.11 g, 1.024 mol).

The crude product (66.25 g) is purified by crystallization from dichloromethane (29.5 g, 0.067 mol, 74%).

$^1$H-NMR {300 MHz, CDCl$_3$, δ (ppm)}: 0.24-2.32 (27 H); 0.85 (s, 3H, CH$_3$-18); 0.89 (s, 3H, CH$_3$-19); 2.56 (s, 1H, OH-17); 3.38 (d, J=6.6 Hz, 1H, OH-3); 3.72-4.15 (m, 6H, H-3, OH, 2×CH$_2$—O); 4.61 (t, J=4.9 Hz, 1H, O—CH—O).

$^{13}$C-NMR {300 MHz, CDCl$_3$, δ (ppm)}: 7.8 (CH$_2$); 11.7 (CH$_2$); 15.3 (CH); 16.1 (CH); 19.1 (CH$_3$); 19.3 (CH$_3$); 21.8 (CH); 22.7 (CH$_2$); 25.3 (CH); 25.7 (CH$_2$); 27.7 (CH$_2$); 29.7 (CH$_2$); 31.0 (CH$_2$); 34.2 (CH); 36.6 (CH$_2$); 40.4 (CH$_2$); 42.7 (C); 43.1 (CH$_2$); 44.9 (C); 52.8 (CH); 53.2 (CH); 66.9 (CH$_2$); 67.0 (CH$_2$); 67.1 (CH); 74.9 (C); 81.9 (C); 102.8 (CH).

HPLC-MS (ESI): [M+Na]$^+$=469; [2M+Na]$^+$=915

EXAMPLE 14

17α-(3,3-dimethoxypropyl)-6β,7β,15β,16β-dimethylen-5β-androstane-3β,5,17β-triol

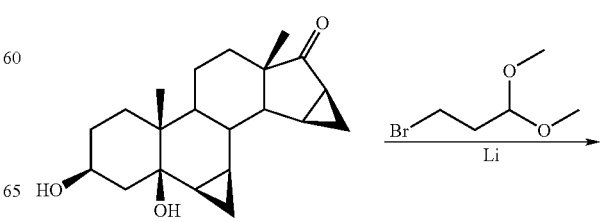

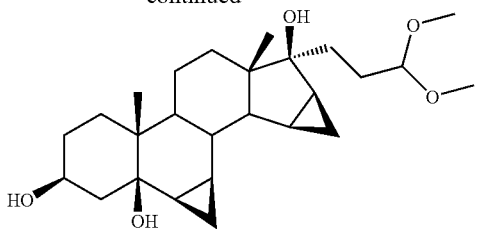

The title compound is prepared according to EXAMPLE 12 by reaction of 3β,5-dihydroxy-6β,7β,15β,16β-dimethylen-5β-androst-17-one (8.21 g, 0.025 mol) with 3-bromo-1,1-dimethoxypropane (31.25 g, 0.171 mol) in the presence of lithium (granular, 2.42 g, 0.348 mol).

The crude product (13.80 g) is purified by column chromatography on silica gel eluting with n-hexane/ethyl acetate to afford the title compound (9.17 g, 0.021 mol, 84%).

$^1$H-NMR {300 MHz, DMSO-d$_s$, δ (ppm)}: 0.13-2.15 (25H); 0.75 (s, 6 H, CH$_3$-18 and CH$_3$-19); 3.21 (s, 6H, 2×OCH$_3$); 3.83 (m, 1H, CH-3); 4.17 (s, 1H, OH); 4.31 (m, 2H, OH and CH—(OMe)$_2$); 4.82 (m, 1H, OH-3).

$^{13}$C-NMR {300 MHz, DMSO, δ (ppm)}: 7.9 (CH$_2$); 11.5 (CH$_2$); 14.5 (CH); 15.8 (CH); 18.9 (CH$_3$); 19.3 (CH$_3$); 21.9 (CH$_2$); 22.1 (CH); 26.5 (CH$_2$); 26.9 (CH$_2$); 28.1 (CH$_2$); 31.6 (CH$_2$); 34.1 (CH); 38.7 (CH$_2$); 40.0 (C); 42.3 (C); 44.0 (CH$_2$); 45.1 (CH); 51.0 (CH$_3$); 52.2 (CH$_3$); 52.7 (CH); 66.0 (CH); 72.9 (C); 80.5 (C); 105.0 (2×CH).

HPLC-MS (ESI): [M+Na]$^+$=457; [2M+Na]$^+$=891

EXAMPLE 15

17α-(2-[1,3]dioxan-2-ylethyl)-6β,7β,15β,16β-dimethylen-5β-androstane-3β,5,17β-triol

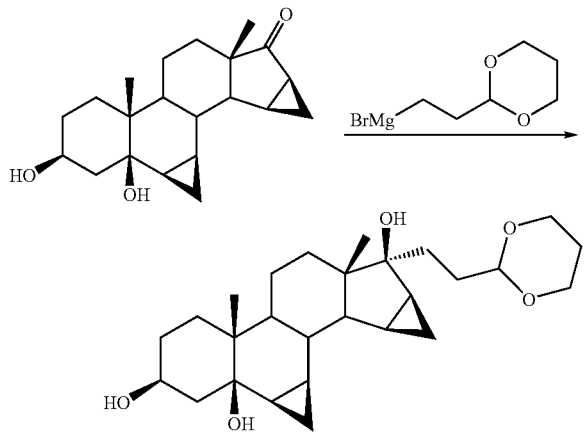

Magnesium turnings (2.35 g, 0.097 mol) are suspended in tetrahydrofuran (8.0 mL) under nitrogen in the presence of a small amount of iodine. 2-(2-Bromoethyl)-[1,3]dioxane (18.88 g, 0.097 mol) diluted in tetrahydrofuran (8.0 mL) is added dropwise at such a rate that the temperature is maintained between 55° C. and 60° C. After one hour the mixture is diluted with tetrahydrofuran (18.0 mL) because of the increased density. Stirring is continued for an additional hour.

A portion (39.39 g) of the prepared solution containing 2-(2-bromomagnesiumethyl)-[1,3]dioxane (16.80 g, 0.077 mol) is added dropwise to 3β,5-dihydroxy-6β,7β,15β,16β-dimethylen-5β-androst-17-one (3.00 g, 0.009 mol) previously dissolved in tetrahydrofuran (39.0 mL) under nitrogen. The mixture is stirred for 3.5 hours monitoring the reaction by TLC analysis. Ice (77.0 g) is then added and stirring continued for 30 minutes. Tetrahydrofuran is removed at 50° C. under reduced pressure and ethyl acetate (60.0 mL) is added followed by celite (15.0 g). The suspension is stirred for 15 minutes at 25° C. After filtering the celite and washing thoroughly with ethyl acetate (50 mL), the two phases are separated and the aqueous one is extracted with ethyl acetate (30 mL). The combined organic layers are washed with water (30 mL) and concentrated at 50° C. under reduced pressure.

The residue is taken up in tetrahydrofuran and concentrated to dryness affording the crude product as a slightly yellow oil (5.35 g).

The title compound is isolated by column chromatography on silica gel eluting with dichloromethane/methanol and obtained as a colorless solid (3.86 g, 0.0086 mol, 95%).

The analytical results correspond to those reported in EXAMPLE 13.

EXAMPLE 16

6β,7β,15β,16β-dimethylen-3-oxo-17α-pregn-4-ene-21,17-carbolactone (Drospirenone)

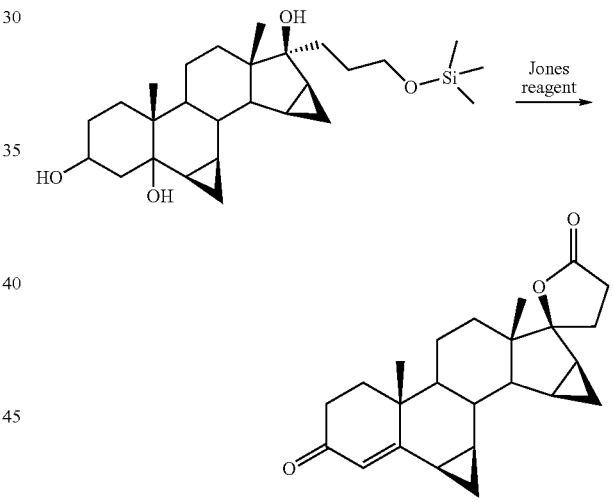

A solution of crude 17α-[3-(trimethylsilanyloxy)-propyl]-6β,7β,15β,16β-dimethylen-5β-androstane-3β,5,17β-triol (0.139 mol) in acetone (1990 mL) and water (81 mL) is cooled to −5-0° C. Jones reagent (431 g containing: 81 g of chromium (VI) oxide, 221 g of water, 127 g of sulfuric acid) is added dropwise at −5/0° C. and the mixture is stirred until TLC analysis reveals that the formation of the product is complete.

The reaction is quenched by addition of ice (933 g), sodium pyrosulfite (503 g), ethyl acetate (933 mL) and stirred for 30 minutes allowing the mixture to reach room temperature. After addition of sodium chloride (477 g) the two phases are separated and the aqueous one is extracted with ethyl acetate (834 mL, 417 mL). The combined organic layers are washed with 10% sodium chloride in water (747 mL, 373 mL), saturated sodium bicarbonate (815 mL, 460 mL), 1M sodium hydroxide (255 mL), saturated sodium bicarbonate (255 mL), water (255 mL). The organic solvent is removed at 50° C. under reduced pressure affording an off-white foam (40.70 g).

The crude product is purified by crystallization from acetone (20.31 g, 0.055 mol, 41%).

Mp: 200° C.

$[\alpha]^{25}_D$ (c=0.5%, CHCl$_3$)=−183°

$^1$H-NMR {200 MHz, CDCl$_3$, δ (ppm)}: 0.8-2.19 (18 H); 0.4-0.6 (m, 1H, cyclopropyl); 1.00 (s, 3H, CH$_3$-18); 1.09 (s, 3H, CH$_3$-19); 2.39-2.61 (m, 4H, 2×CH$_2$—C=O); 6.05 (s, 1H, H-4).

$^{13}$C-NMR {200 MHz, CDCl$_3$, δ (ppm)}: 9.7 (CH$_2$); 16.5 (CH); 17.4 (CH$_2$); 18.7 (CH$_3$); 18.8 (CH); 19.5 (CH); 19.6 (CH$_2$); 20.7 (CH$_3$); 24.2 (CH); 29.1 (CH$_2$); 30.5 (CH$_2$); 33.8 (CH$_2$); 34.0 (CH); 36.9 (CH$_2$); 37.2 (CH$_2$); 41.5 (C); 51.5 (CH); 51.6 (CH); 95.9 (C); 103.8 (C); 125.6 (CH); 171.1 (C); 176.4 (C); 197.6 (C).

HPLC-MS (ESI): [M+H]$^+$=367; [2M+Na]$^+$=755

EXAMPLE 17

6β,7β,15β,16β-Dimethylen-3-oxo-17α-pregn-4-ene-21,17-carbolactone (Drospirenone)

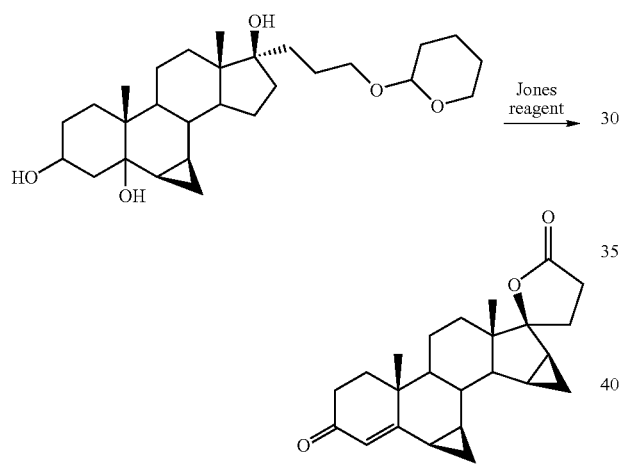

The preparation of the title compound is analogous to the one reported in EXAMPLE 16 starting from 17α-[3-(tetrahydropyran-2-yloxy)propyl]-6β,7β,15β,16β-dimethylen-5β-androstane-3β,5,17β-triol (5.01 g, 0.011 mol).

Crude product (3.10 g) is crystallized from acetone (2.01 g, 0.005 mol, 51%).

Analytical data correspond to those reported in EXAMPLE 16.

EXAMPLE 18

6β,7β,15β,16β-Dimethylen-3-oxo-17α-pregn-4-ene-21,17-carbolactone (Drospirenone)

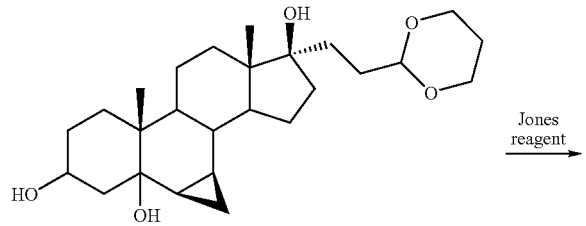

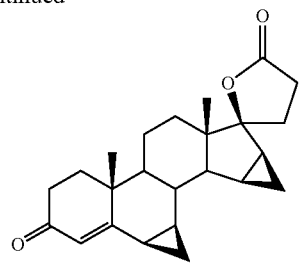

The preparation is analogous to the one reported in EXAMPLE 16 starting from 17α-(2-[1,3]dioxan-2-ylethyl)-6β,7β,15β,16β-dimethylen-5β-androstane-3β,5,17β-triol (58.11 g, 0.130 mol).

The crude product (42.79 g) is filtered through silica gel washing with dichloromethane/methanol. After removing the solvents, crystallization of the solid from acetone affords pure drospirenone (15.03 g, 0.041 mol, 32%).

Analytical data correspond to those reported in EXAMPLE 16.

EXAMPLE 19

6β,7β,15β,16β-Dimethylen-3-oxo-17α-pregn-4-ene-21,17-carbolactone (Drospirenone)

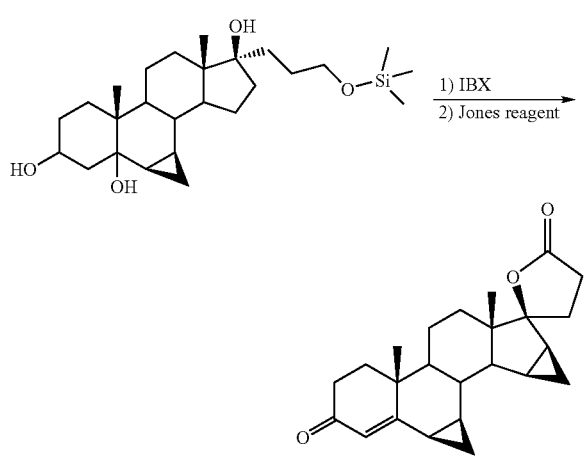

Crude 17α-[3-(trimethylsilanyloxy)propyl]-6β,7β,15β,16β-dimethylen-5β-androstane-3β,5,17β-triol (0.111 mol) is dissolved in dimethylsulfoxide (1012 mL) and IBX (88.66 g, 0.317 mol; prepared according to the procedure reported in J. Org. Chem., 64 (1999), 4537-4538) is added portionwise at 20° C. The mixture is vigorously stirred for 20 hours monitoring the conversion by TLC analysis. After diluting with ethyl acetate (1000 mL), water (1012 mL) is slowly added and the thick mixture is stirred over 15 minutes. The solid is filtered and washed with ethyl acetate. After adding sodium chloride (100 g) to the filtrate, the collected phases are separated. The aqueous layer is extracted twice with ethyl acetate (900 mL, 600 mL) and the combined organic layers are washed with brine (550 mL), 0.1 N sodium hydroxide (800 mL) and water (700 mL). The organic solution is concentrated at 50° C. under reduced pressure, the residue is taken up in tetrahydrofuran and concentrated again. The solid is suspended in diisopropyl ether (250 mL) and stirred at 0-5° C. for 1 hour. Filtration affords a solid which is dried at 45° C. in a vacuum oven to constant weight (40.00 g).

A solution of the solid in acetone (1200 mL) and water (48 mL) is cooled to 0-5° C. Jones reagent (141.80 g, containing: 26.8 g of chromium (VI) oxide, 73 g of water, 42 g of sulfuric acid) is added dropwise at 0-5° C. and the mixture is stirred until TLC analysis reveals that the formation of the product is complete.

The reaction is quenched by addition of ice (400 g), ethyl acetate (574 mL) and sodium pyrosulfite (167 g), and stirring is continued for 30 minutes. After the addition of sodium chloride (45 g) the two phases are separated and the aqueous one is extracted with ethyl acetate (500 mL). The combined organic layers are washed once with 10% sodium chloride in water (500 mL), 1N sodium hydroxide (400 mL), saturated sodium bicarbonate (400 mL) brine (500 mL) and water (300 mL).

Ethyl acetate is removed under reduced pressure and the residue is dissolved in dichloromethane (110 mL) and washed with brine (300 mL). After drying over sodium sulfate, the organic solvent is removed at 50° C. under reduced pressure affording an off-white foam (33.26 g). Trituration with diisopropylether (750 mL) gives 31.00 g of the product.

After crystallization from acetone drospirenone is obtained (20.92 g, 0.057 mol, 51%).

Analytical data correspond to the ones reported in EXAMPLE 16.

EXAMPLE 20

6β,7β,15β,16β-Dimethylen-3-oxo-17α-pregn-4-ene-21,17-carbolactone (Drospirenone)

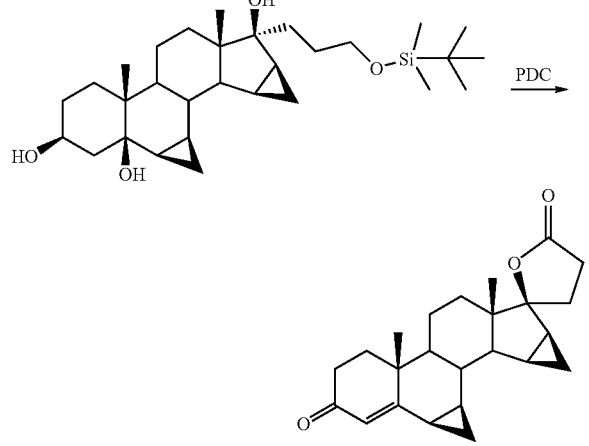

(17α-[3-(tert-Butyldimethylsilanyloxy)propyl]-6β,7β,15β,16β-dimethylen-5β-androstane-3β,5,17β-triol (0.39 g, 0.001 mol) is dissolved in N,N-dimethylformamide (7 mL) and is treated with pyridinium dichromate (2.30 g, 0.006 mol). The reaction is stirred for two hours at 20° C. and subsequently heated up to 50° C. for three hours.

A saturated sodium sulfite solution (15 mL) is then added and the mixture is extracted with ethyl acetate (15 mL). When the colour turns completely into green, the organic phase is separated, washed twice with water (2×10 mL) and dried over sodium sulfate. Removal of the solvent under reduced pressure affords the crude product (0.30 g) which is purified on silica gel affording the title compound (0.24 g, 0.0006 mol, 65%).

Analytical data correspond to the ones reported in EXAMPLE 16.

EXAMPLE 21

17α-[3-(tert-Butyl-dimethylsilanyloxy)propyl]-6β,7β,15β,16β-dimethylenandrost-4-en-17β-ol-3-one

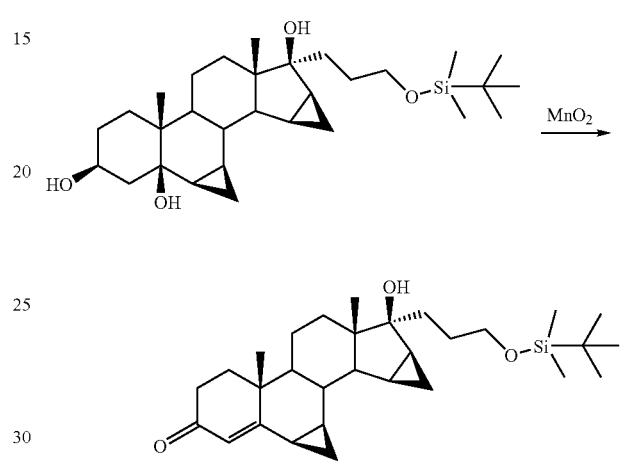

17α-[3-(tert-butyldimethylsilanyloxy)propyl]-6β,7β,15β,16β-dimethylen-5β-androstane-3β,5,17β-triol (0.058 mol) is dissolved in toluene (924 mL) at 80° C. and manganese (IV) dioxide (90%, 223.50 g, 2.314 mol) is added portionwise. After 6 hours an additional amount of oxidant is added (20.30 g, 0.210 mol). When the reaction is complete according to TLC analysis, ethyl acetate (460 mL) and water (1850 mL) are added. Oxalic acid (417.00 g) is then added portionwise over 50 minutes while maintaining the temperature below 10° C. The mixture is vigorously stirred and the development of carbon dioxide is observed. After allowing the system to reach 20° C., the two phases are separated. The aqueous layer is extracted twice with ethyl acetate (460 mL, 230 mL) and the combined organic layers are washed with water (460 mL, 230 mL) and saturated sodium bicarbonate (460 mL, 230 mL).

After removing the solvent of the organic phase at 60° C. under reduced pressure, the crude product is obtained. (29.00 g, quantitative yield).

A sample is purified by column chromatography, eluting with n-hexane/ethyl acetate, and analyzed.

$^1$H-NMR {200 MHz, CDCl$_3$, δ (ppm)}: 0.84-1.95 (20 H); 0.08 (s, 6H, 3 Si(CH$_3$)$_2$); 0.31 (m, 1H, cyclopropyl(CH$_2$)); 0.91 (s, 9H, C(CH$_3$)); 0.93 (s, 3H, CH$_3$-18); 1.10 (s, 3H, CH$_3$-19); 2.26-2.68 (m, 3H, CH$_2$—C═O, OH); 3.70 (m, 2H, —CH$_2$O); 6.02 (s, 1H, H-4);

$^{13}$C-NMR {200 MHz, CDCl$_3$, δ (ppm)}: −5.4 (2×CH$_3$); 7.7 (CH$_2$); 15.8 (CH); 17.4 (CH$_3$); 18.2 (C); 18.9 (CH$_2$); 19.0 (CH); 19.1 (CH$_3$); 20.1 (CH); 21.1 (CH$_2$); 23.0 (CH); 25.9 (3×CH$_3$); 27.0 (CH$_2$); 33.7 (CH$_2$); 33.9 (CH$_2$); 34.7 (CH); 36.4 (CH$_2$); 36.9 (CH$_2$); 37.4 (C); 42.4 (CH); 52.0 (CH); 52.5 (CH); 63.8 (CH$_2$); 81.6 (C); 125.5 (CH); 172.1 (C); 198 (C).

HPLC-MS (ESI): [M+H]⁺=485; [M+Na]⁺=507; [2M+Na]⁺=991

EXAMPLE 22

17α-[3-Hydroxypropyl]-6β,7β,15,16β,-dimethylenandrost-4-en-17β-ol-3-one

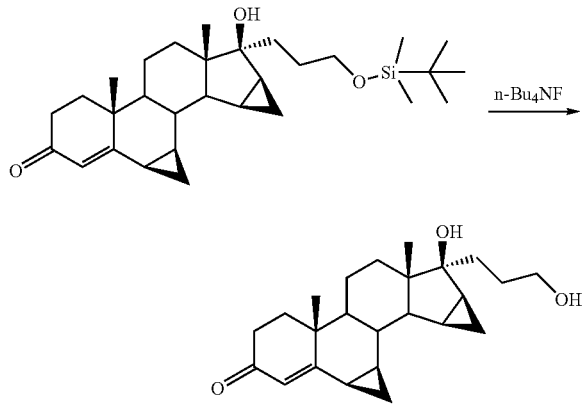

A solution of 17α-[3-tert-butyldimethylsylanyloxypropyl]-6β,7β,15β,16β-dimethylen-androst-4-en-17β-ol-3-one (29.00 g, 0.058 mol) in tetrahydrofuran (435 mL) is treated at 20° C. with tetra-n-butylammonium fluoride trihydrate (9.18 g, 0.029 mol). Two additional portions of fluoride are added after 50 minutes (0.92 g, 0.003 mol) and after 80 minutes (1.84 g, 0.006 mol) respectively.

After three hours stirring no more starting material is visible on TLC and the reaction is quenched by pouring the mixture into 24% sodium chloride aqueous solution (650 mL). Stirring is continued for 15 minutes and the phases are subsequently separated.

The aqueous layer is extracted with ethyl acetate (250 mL) and the combined organic phases are washed twice with brine (2×250 mL) and concentrated under reduced pressure at 50° C. The dark brown oil thus obtained is taken up in tetrahydrofuran (100 mL) and concentrated again.

The residue (24.61 g) is suspended in diisopropylether/n-hexane (22 mL/224 mL), the mixture is stirred for 30 minutes at 0° C. and filtered. The solid is washed with n-hexane (25 mL). The sequence is repeated twice stirring at 20° C.

The solid is dried at 50° C. in a vacuum oven to constant weight (15.50 g).

Further purification by column chromatography, eluting with ethyl acetate/methanol, affords the title compound (7.94 g, 0.021 mol, 37%).

$^1$H-NMR {300 MHz, CDCl$_3$, δ (ppm)}: 0.32-2.62 (25H); 0.92 (s, 3H, CH$_3$-18); 1.09 (s, 3H, CH$_3$-19); 3.72 (m, 2H, CH$_2$—O); 6.01 (s, 1H, H-4).

$^{13}$C-NMR {300 MHz, CDCl$_3$, δ (ppm)}: 7.8 (CH$_2$); 16.0 (CH); 17.5 (CH$_3$); 18.9 (CH$_2$); 19.0 (CH); 19.2 (CH); 20.1 (CH); 21.1 (CH$_2$); 22.7 (CH); 27.0 (CH$_2$); 33.8 (CH$_2$); 33.9 (CH$_2$); 34.7 (C); 36.3 (CH); 37.0 (CH$_2$); 37.4 (CH$_2$); 42.5 (C); 52.0 (CH); 52.5 (CH); 63.3 (CH$_2$); 82.0 (C); 125.5 (CH); 172.2 (C); 198.1 (C).

HPLC-MS (ESI): [M+H]⁺=371; [M+K]⁺=409; [2M+Na]⁺=763

EXAMPLE 23

6β,7β,15β,16β-Dimethylen-3-oxo-17α-pregn-4-ene-21,17-carbolactone (Drospirenone)

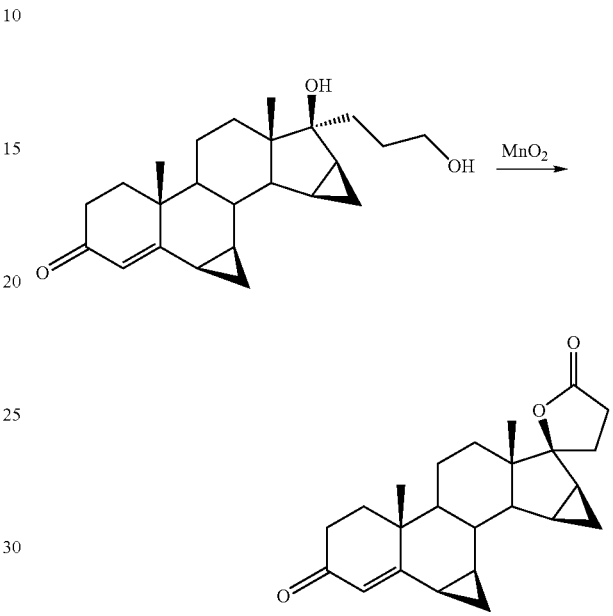

17α-[3-Hydroxypropyl]-6β,7β,15β,16β-dimethylen-androst-4-en-17β-ol-3-one (0.50 g, 0.001 mol) is dissolved in tetrahydrofuran (10 mL) at 55° C. and manganese (IV) dioxide (90%, 2.50 g, 0.026 mol) is added portionwise. After 6 hours an additional amount of oxidant (90%, 1.25 g, 0.013 mol) is added. When the reaction is complete according to TLC analysis, tetrahydrofuran (100 mL) is added and the mixture is filtered. The filtrate is concentrated at 50° C. under reduced pressure affording the crude product (0.34 g). The title compound is isolated by column chromatography, eluting with n-hexane/ethyl acetate. (0.20 g, 0.0005 mol, 50%).

Analytical are in agreement with those reported in EXAMPLE 16.

EXAMPLE 24

17α-[3-Hydroxypropyl]-6β,7β,15β,16β-dimethylenandrostan-3β,5,17β-triol

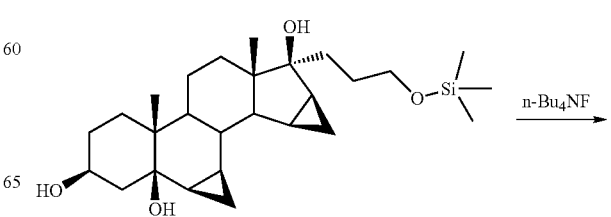

-continued

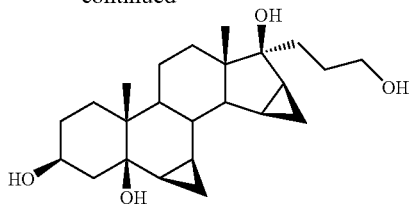

17α-[3-(tert-Butyldimethylsilanyloxy)propyl]-6β,7β,15β,16β-dimethylen-5β-androstane-3β,5,17β-triol (0.059 mol) dissolved in tetrahydrofuran (200 mL) is treated at 0-5° C. with a solution of tetra-n-butylammonium fluoride trihydrate (9.18 g, 0.029 mol) in tetrahydrofuran (100 mL). After 20 minutes no more starting material is visible by TLC analysis and the reaction is quenched by pouring the mixture into water/ice (200 g/145 g). Sodium chloride (20 g) is added and the mixture is extracted with ethyl acetate (190 mL). The phases are subsequently separated; the organic layer is washed with brine (200 mL, 100 mL) and concentrated at 50° C. under reduced pressure. The dark brown oil obtained is taken up in tetrahydrofuran (100 mL) and concentrated again.

The residue (29.39 g) is crystallized from acetone giving the title compound (15.07 g, 0.040 mol, 67%).

$^1$H-NMR {200 MHz, DMSO-d$_6$, δ (ppm)}: 0.17 (m, 1H, cyclopropyl(CH$_2$)); 0.38-2.17 (24H); 0.76 (s, 6H, (CH$_3$-18 and CH$_3$-19)); 3.48 (m, 2H, CH$_2$—OH); 3.84 (m, 1H, H-3); 4.13 (s, 1H, OH); 4.39 (m, 2H, 2×OH); 4.83 (d, J=3.8 Hz, 1H, OH-3).

$^{13}$C-NMR {200 MHz, DMSO-d$_6$, δ (ppm)}: 7.9 (CH$_2$); 14.5 (CH); 15.8 (CH); 18.9 (CH$_3$); 19.4 (CH$_3$); 22.0 (CH$_2$); 22.2 (CH); 22.8 (CH); 27.0 (CH$_2$); 27.3 (CH$_2$); 27.7 (CH$_2$); 33.5 (CH$_2$); 34.2 (CH); 36.5 (CH$_2$); 40.0 (C); 42.4 (C); 43.9 (CH$_2$); 52.8 (CH); 62.1 (CH$_2$); 63.9 (CH$_2$); 66.8 (CH); 67.9 (CH); 72.9 (C); 80.8 (C).

HPLC-MS (ESI): [(M−H$_2$O)+H]$^+$=373

EXAMPLE 25

6β,7β,15β,16β-Dimethylen-3-oxo-17α-pregn-4-ene-21,17-carbolactone (Drospirenone)

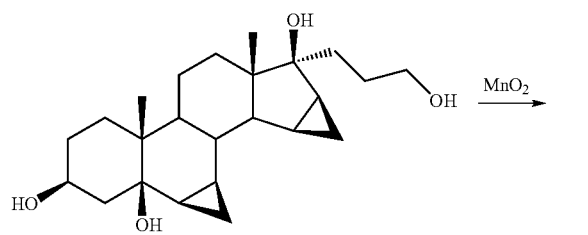

17α-(3-Hydroxypropyl)-6β,7β,15β,16β-dimethylenandrostan-3β,5,17β-triol (3.00 g, 0.008 mol) is dissolved in toluene (140 mL) at reflux and manganese (IV) dioxide (90%, 15.00 g, 0.155 mol) is added portionwise. After 6 hours at 82-85° C. an additional amount of oxidant is added (90%, 3.00 g, 0.031 mol). When the reaction is complete according to TLC analysis, the mixture is cooled to room temperature and water (185 mL) and ethyl acetate (120 mL) are added. Manganese dioxide is quenched by adding oxalic acid (40.00 g) portionwise while the temperature is maintained below 10° C. The mixture is vigorously stirred and development of carbon dioxide is observed. After allowing the system to reach 20° C., the mixture is filtered washing with ethyl acetate. The collected phases are separated, the aqueous layer is extracted with ethyl acetate (100 mL) and the combined organic layers are washed with water (75 mL), saturated sodium bicarbonate (100 mL) and brine (75 mL, 55 mL).

After removing the organic solvent at 50° C. under reduced pressure, the crude product is obtained as a yellow foam (2.05 g).

Recrystallization from acetone affords the title compound (1.14 g, 0.003 mol, 37%)

Analytical data are in agreement with the ones reported in EXAMPLE 16.

EXAMPLE 26

17α-(2-[1,3]Dioxan-2-ylethyl)-6β,7β,15β,16β-dimethylenandrost-4-en-17β-ol-3-one

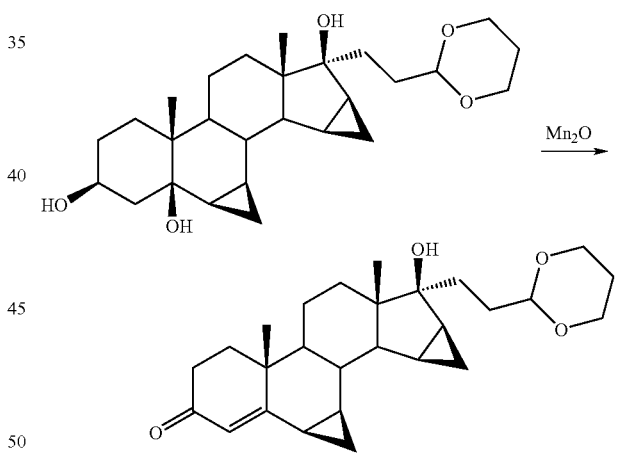

17α-(2-[1,3]-Dioxan-2-ylethyl)-6β,7β,15β,16β-dimethylen-5β-androstane-3β,5,17β-triol (14.25 g, 0.032 mol) is dissolved in toluene (550 mL) at reflux and manganese (IV) dioxide (90%, 57.00 g, 0.611 mol) is added portionwise. After stirring for 5 hours at 82-85° C. an additional amount of oxidant is added (90%, 5.00 g, 0.052 mol). When the reaction is complete according to TLC analysis, the mixture is cooled to room temperature and water (900 mL) and ethyl acetate (350 mL) are added. Manganese dioxide is quenched by adding oxalic acid (116.00 g) portionwise while the temperature is maintained below 10° C. The mixture is vigorously stirred and development of carbon dioxide is observed. The solid is filtered washing thoroughly with ethyl acetate. The two collected phases are separated and the aqueous layer is extracted with ethyl acetate (300 mL). The combined organic layers are washed with water (500 mL), saturated sodium bicarbonate (400 mL) and water (2×300 mL).

After removing the organic solvent at 50° C. under reduced pressure, the product is obtained as an orange oil (15.73 g).

The title compound is isolated by column chromatography eluting with n-hexane:ethyl acetate (10.23 g, 0.024 mol, 75%).

$^1$H-NMR {200 MHz, CDCl$_3$, δ (ppm)}: 0.38 (s, 1H, cyclopropyl(CH$_2$)); 0.82-2.68 (25H); 0.93 (s, 3H, CH$_3$-18); 1.10 (s, 3H, CH$_3$-19); 3.7-3.85 (m, 2H, CH$_2$—O); 4.10-4.18 (m, 2H, CH$_2$—O); 4.62 (t, J=4.4 Hz, 1H, O—CH—O); 6.01 (s, 1H, H-4).

$^{13}$C-NMR {200 MHz, CDCl$_3$, δ (ppm)}: 7.8 (CH$_2$); 15.9 (CH); 17.5 (CH); 18.9 (CH$_3$); 19.0 (CH$_2$); 19.1 (CH$_3$); 20.1 (CH$_2$); 21.1 (CH$_2$); 22.9 (CH); 25.7 (CH); 29.7 (CH$_2$); 31.0 (CH$_2$); 33.9 (CH$_2$); 34.7 (CH); 36.4 (CH$_2$); 37.0 (CH$_2$); 37.4 (C); 42.5 (C); 51.9 (CH); 52.4 (CH); 66.9 (2×CH$_2$); 81.7 (C); 102.6 (CH); 125.6 (CH); 172.0 (C); 198.0 (C).

HPLC-MS (ESI): [M+H]$^+$=427; [2M+Na]$^+$=875

EXAMPLE 27

17α-(2-[1,3]Dioxolan-2-ylethyl)-6β,7β,15β,16β-dimethylenandrost-4-en-17β-ol-3-one

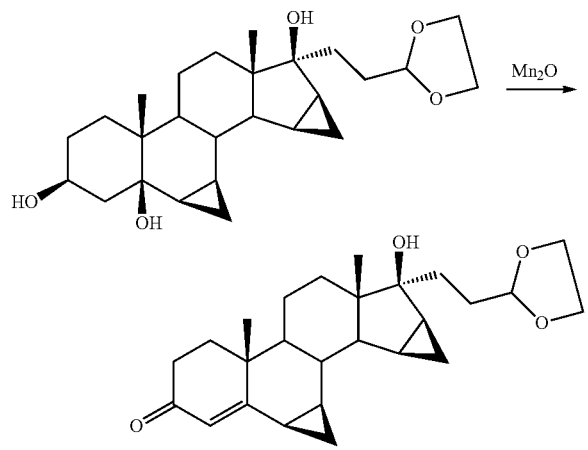

The preparation of the title compound is analogous to the one reported in EXAMPLE 26 starting from 17α-(2-[1,3]dioxolan-2-yl-ethyl)-6β,7β,15β,16β-dimethylen-5β-androstane-3β,5,17β-triol (30.00 g, 0.069 mol).

The crude product is a mixture of 17α-(2-[1,3]-dioxolan-2-yl-ethyl)-6β,7β,15β,16β-dimethylen-androst-4-en-17β-ol-3 and drospirenone (HPLC analysis shows a ratio 65:25 at 266 nm).

Column chromatography on silica gel performed on 15.63 g of crude product affords 0.66 g of drospirenone (0.002 mol), 5.05 g di 17α-(2-[1,3]dioxolan-2-ylethyl)-6β,7β;15β,16β-dimethylenandrost-4-en-17β-ol-3-one and 6.04 g of the mixture of the two products.

$^1$H-NMR {200 MHz, CDCl$_3$, δ (ppm)}: 0.8-2.62 (14H); 0.94 (s, 3H, CH$_3$-18); 1.10 (s, 3H, CH$_3$-19); 3.90 (m, 2H, O—CH$_2$); 4.02 (m, 2H, O—CH$_2$); 4.96 (t, J=4.5 Hz, 1H, O—CH—O); 6.02 (s, 1H, H-4).

$^{13}$C-NMR {200 MHz, CDCl$_3$, δ (ppm)}: 7.7 (CH$_2$); 15.0 (CH); 16.0 (CH$_3$); 17.5 (CH$_3$); 18.8 (CH); 18.9 (CH$_2$); 20.1 (CH); 21.1 (CH$_2$); 22.8 (CH); 28.2 (CH$_2$); 30.7 (CH$_2$); 33.9 (CH$_2$); 34.7 (CH); 36.0 (CH$_2$); 36.3 (C); 37.4 (CH$_2$); 42.5 (C); 51.9 (CH); 54.4 (CH); 68.8 (2×CH$_2$); 81.7 (C); 104.8 (CH); 125.5 (CH); 172.1 (C); 184.3 (C).

HPLC-MS (ESI): [M+H]$^+$=413; [2M+Na]$^+$=847

EXAMPLE 28

17α-(3,3-Dimethoxypropyl)-6β,7β,15β,16β-dimethylen-androst-4-en-17β-ol-3-one

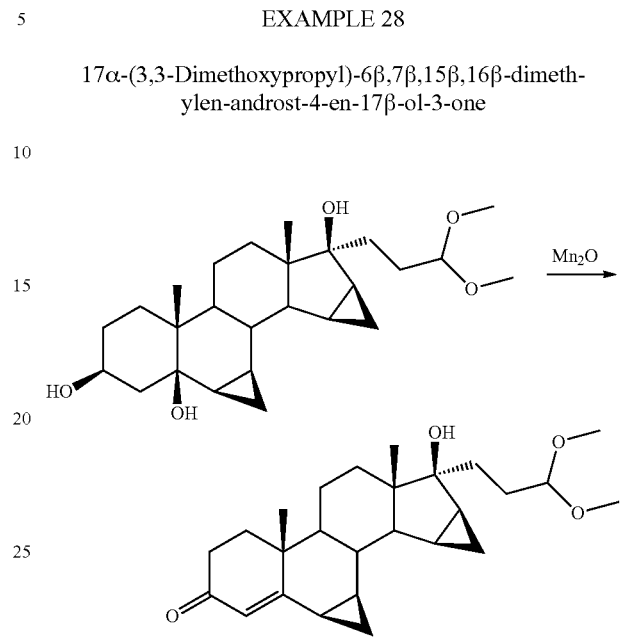

The preparation of the title compound is analogous to the one reported in EXAMPLE 26 starting from 17α-(3,3-dimethoxypropyl)-6β,7β,15β,16β-dimethylen-5β-androstan-3β,5,17β-triol (8.39 g, 0.019 mol). 5.50 g of crude product is obtained.

A sample of the product is isolated by column chromatography eluting with dichloromethane/methanol.

$^1$H-NMR {200 MHz, CDCl$_3$, δ (ppm)}: 0.32 (m, 1H, cyclopropyl(CH$_2$)); 0.65 (s, 3H, CH$_3$-18); 0.80-2.14 (20H); 0.82 (s, 3H, CH$_3$-19); 2.22-2.55 (m, 3H, CH$_2$—C=O, OH); 3.34 (s, 6H, 2×(OCH$_3$)); 4.40 (t, J=5.6 Hz, 1H, O—CH—O); 6.00 (s, 1H, H-4).

$^{13}$C-NMR {200 MHz, CDCl$_3$, δ (ppm)}: 7.7 (CH$_2$); 15.2 (CH); 16.0 (CH$_3$); 17.5 (CH$_3$); 18.9 (CH); 19.0 (CH$_2$); 20.1 (CH); 21.1 (CH$_2$); 22.9 (CH); 27.1 (CH$_2$); 31.5 (CH$_2$); 33.9 (CH$_2$); 34.7 (CH); 36.3 (C); 37.0 (CH$_2$); 37.3 (CH$_2$); 42.4 (C); 51.9 (CH); 52.5 (CH); 53.0 (2 CH$_3$); 81.3 (C); 105.3 (CH); 125.6 (CH); 171.9 (C); 198.0 (C).

HPLC-MS (ESI): [M+H]$^+$=415; [M+Na]$^+$=437 [2M+Na]$^+$=851

EXAMPLE 29

6β,7β,15β,16β-Dimethylen-3-oxo-17α-pregn-4-ene-21,17-carbolactone (Drospirenone)

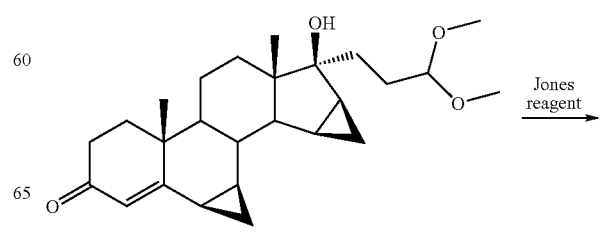

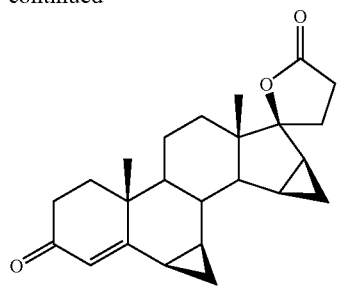

17α-(3,3-Dimethoxypropyl)-6β,7β,15β,16β-dimethyl-enandrost-4-en-17β-ol-3-one (0.434 g, 0.001 mol) is dissolved in 1,2-dimethoxyethane (10 mL) at room temperature. Jones reagent (1.27 containing: 0.24 g of chromium (VI) oxide, 0.65 g of water, 0.38 g of sulfuric acid) is added dropwise and the reaction is monitored by TLC. After 4 hours ethyl acetate is added (20 mL) followed by a saturated solution of sodium pyrosulfite (15 mL). The mixture is stirred for 15 minutes and the two phases are separated; the organic one is washed with water (2×10 mL) and is concentrated at 50° C. under reduced pressure.

The desired product is purified by column chromatography on silica gel (0.28 g, 0.0008 mol, 76%).

Analytical data correspond to those reported in EXAMPLE 16.

EXAMPLE 30

6β,7β,15β,16β-Dimethylen-3-oxo-17α-pregn-4-ene-21,17-carbolactone (Drospirenone)

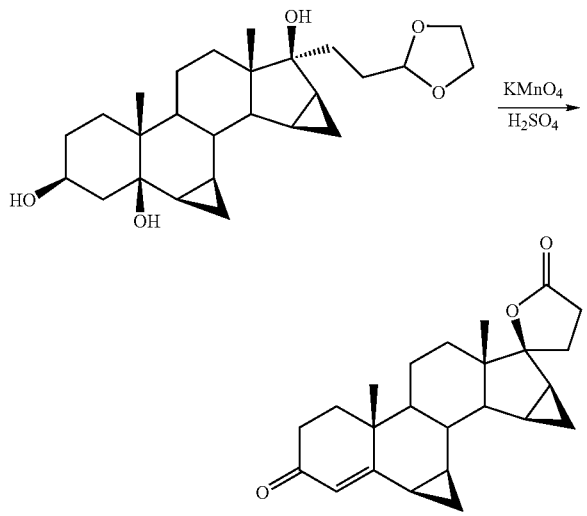

17α-(2-[1,3]Dioxolan-2-yl-ethyl)-6β,7β,15β,16β-dimethylen-5β-androstan-3β,5,17β-triol (1.50 g, 0.003 mol) is dissolved in acetone (36 mL) at 25° C. A solution of potassium permanganate (1.10 g, 0.007 mol) in a water/acetone mixture (6.6 mL/13.8 g) is added dropwise followed by sulfuric acid (96%, 0.20 mL, 0.004 mol); the temperature rises to 35° C. and the mixture is kept in a water bath.

Some additional portions of potassium permanganate (3.33 g, 0.021 mol) are added together with sulfuric acid (1.12 mL, 0.021 mol). At the end of the reaction (checked by TLC analysis) ethyl acetate is added (100 mL) followed by water/ice (70 g/70 g), oxalic acid (3.12 g, 0.035 mol) and sodium pyrolsulfite (3.80 g, 0.020 mol); the resulting mixture is stirred at 0-5° C. for 15 minutes. After filtering the colourless solid off, the phases are separated and the aqueous layer is extracted with ethyl acetate (70 mL). The combined organic layers are washed with brine (50 mL), saturated sodium bicarbonate (70 mL, 50 mL), water (50 mL) and concentrated at 45° C. under reduced pressure giving a colourless semisolid (0.6 g).

The product is isolated by column chromatography on silica gel eluting with n-hexane:ethyl acetate) (0.4 g, 0.001 mol, 33%).

Analytical data correspond to those reported in EXAMPLE 16.

EXAMPLE 31

6β,7β,15β,16β-Dimethylen-3-oxo-17α-pregn-4-ene-21,17-carbolactone (Drospirenone)

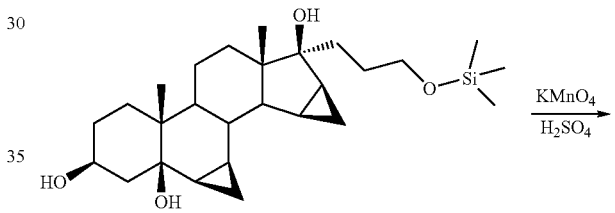

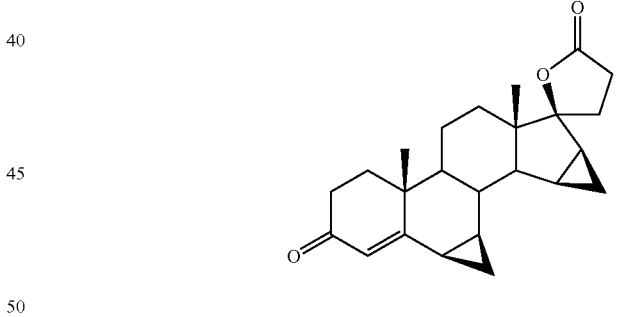

The preparation of the title compound is analogous to the one reported in EXAMPLE 27 starting from 6.30 g (0.009 mol) of crude (17α-[3-(tert-butyldimethylsilanyloxy)propyl]-6β,7β,15β,16β-dimethylene-5β-androstane-3β,5,17β-triol which is reacted with potassium permanganate (7.43 g, 0.047 mol) and 3M sulphuric acid (7.8 mL, 0.023 mol).

After purification by column chromatography the title compound is obtained (0.44 g, 0.0012 mol, 13%).

Analytical data correspond to the ones reported in EXAMPLE 16.

The invention claimed is:

1. A process for the preparation of 6β,7β,15β,16β-dimethylen-3-oxo-17α-pregn-4-ene-21,17-carbolactone (I) which comprises the following steps:

1) reacting compound 6

*[Structure of compound 6: steroid with 3β-OH, 5-OH, 17-ketone, with cyclopropane rings]* with a compound of formula II:

$$X\diagdown\diagup\diagdown R \qquad II$$

wherein X is halogen and R- is a group selected from the group consisting of:

a) —CH$_2$—OR$^I$, wherein R$^I$ is a hydroxyl-protecting group; and b)

$$\text{—CH(OR}^{II}\text{)(OR}^{III}\text{)}$$

wherein R$^{II}$ and R$^{III}$, independently from one another, are (C$_1$-C$_3$)alkyl or R$^{II}$ and R$^{III}$, together with the oxygen atoms they are attached to, form a 1,3-dioxane or 1,3-dioxolane;

to obtain compound 8:

*[Structure of compound 8: steroid with 3β-OH, 5-OH, 17-OH, 17-CH₂CH₂-R side chain, with cyclopropane rings]*

2) oxidating compound 8 with removal of protecting groups R$^I$, R$^{II}$ or R$^{III}$ to obtain drospirenone I:

*[Structure of compound 8 shown again with arrow]*

*[Structure of drospirenone I: steroid with 3-ketone, Δ4, spirolactone, cyclopropane rings]*

2. A process according to claim 1, wherein the hydroxyl-protecting group R$^I$ is one of the following:

i) a silyl derivative Q$_3$Si—, wherein Q, independently from one another, represents (C$_1$-C$_6$)alkyl, (C$_6$-C$_{10}$)aryl, (C$_1$-C$_4$)alkylaryl or (C$_1$-C$_4$)alkoxyaryl, or ii)

*[cyclic acetal structure with (CH$_2$)$_n$]* wherein n is 1 or 2.

3. A process according to claim 1, wherein in said compound II X is halogen and R$^I$ is a silyl derivative Q$_3$Si—, wherein Q, independently from one another, represents (C$_1$-C$_6$)alkyl, (C$_6$-C$_{10}$)aryl, (C$_1$-C$_4$)alkylaryl or (C$_1$-C$_4$)alkoxyaryl.

4. A process according to claim 1, wherein step (1) is carried out in an aprotic solvent in the presence of lithium.

5. A process according to claim 1, which further comprises transforming compound II into the corresponding alkyl-magnesium compound prior to its reaction with compound 6.

6. A process according to claim 1, wherein step (2) is carried out with a Cr$^{VI}$ or Mn$^{IV/VII}$-base oxidant.

7. A process according to claim 6, wherein said Cr$^{VI}$ or Mn$^{IV/VII}$-based oxidant is selected from the group consisting of:

i) CrO$_3$ (Jones reagent);

ii) Pyridinium-dichromate;

iii) MnO$_2$; and iv) KMnO$_4$.

8. A process according to claim 1, wherein in step 2) compound 8 is oxidized, and any protecting group removed therefrom, in a one-step reaction using CrO$_3$.

9. A process according to claim 8, wherein said oxidation is performed first by reaction with o-iodoxybenzoic acid (IBX) followed by treatment with CrO$_3$.

10. A process according to claim 1, wherein in step 2) compound 8 is oxidized with manganese dioxide, to obtain intermediate 9:

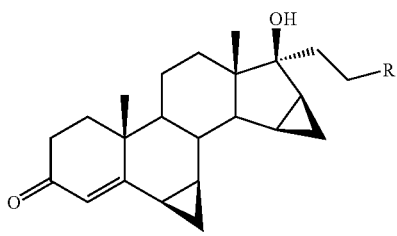

9 which is then deprotected and oxidized to lactone with CrO₃, to yield drospirenone.

11. A process according to claim 1, wherein in step 2) compound 8, in which R=CH₂—OR$^I$ wherein R$^I$ is Q₃Si— and Q independently from one another, represents (C₁-C₆)alkyl, (C₆-C₁₀)aryl, (C₁-C₄)alkylaryl or (C₁-C₄)alkoxyaryl, is first oxidized with manganese dioxide, to yield intermediate 9, wherein said intermediate 9 is then hydrolized to remove the R$^I$ group, to yield intermediate 10:

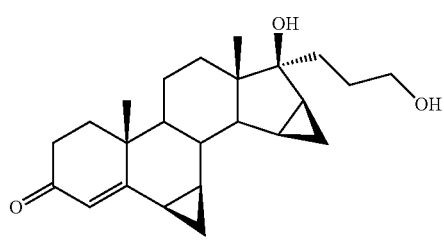

10 wherein said intermediate 10 is oxidized to lactone with manganese dioxide, to yield drospirenone.

12. A process according to claim 1, wherein in step 2) compound 8, in which R=—CH₂—OR$^I$ wherein R$^I$ is Q₃Si— and Q independently from one another, represents (C₁-C₆)alkyl, (C₆-C₁₀)aryl, (C₁-C₄)alkylaryl or (C₁-C₄)alkoxyaryl, is hydrolysed to give intermediate 11:

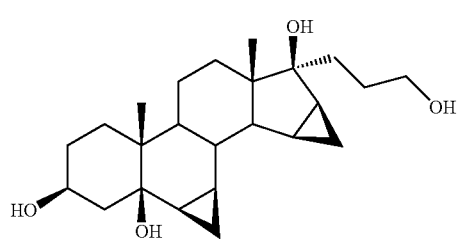

11 wherein said intermediate 11 is oxidized with manganese dioxide to yield drospirenone.

13. A process according to claim 1, further comprising the following steps for preparing 3β,5-dihydroxy-6β,7β,15β,16β-dimethylen-5β-androstan-17-one (compound 6):

a) epoxydazing 7β-hydroxy-15β,16β-methylen-3β-pivaloyloxy-5-androsten-17-one (1) with tert-butylhydroperoxide in the presence of vanadyl acetylacetonate in toluene at 70-75° C., to give 5,6β-epoxy-7β-hydroxy-15β,16β-methylen-3β-pivaloyloxy-5β-androstan17-one 2:

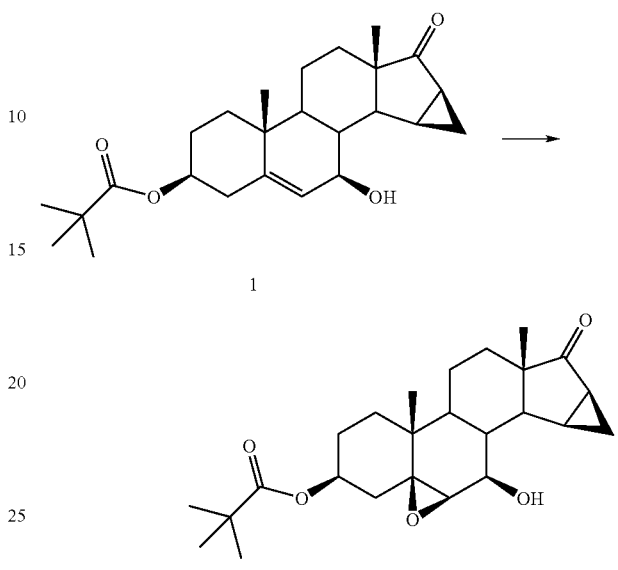

b) reacting compound 2 with hexachloroacetone in dichloromethane added with triphenylphosphine at a temperature of 0-5° C. followed by heating to 10-15° C., to yield 7α-chloro-5,6β-epoxy-15β,16β-methylen-3β-pivaloyloxy-5β-androstan-17-one 3:

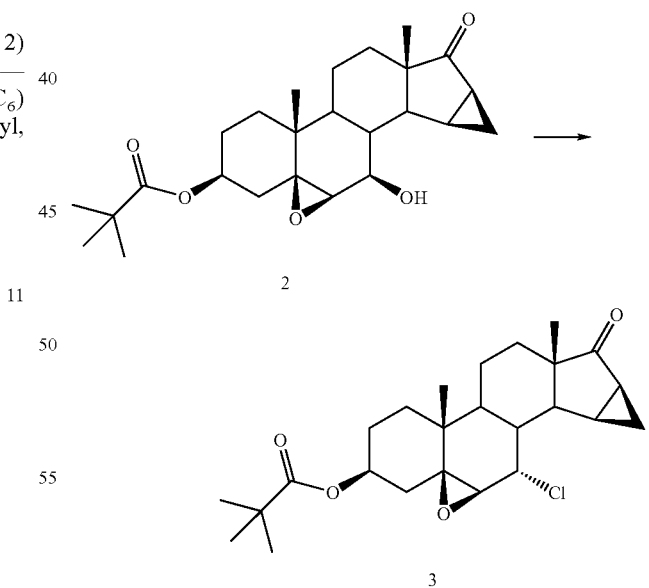

c) reacting compound 3 with acetic acid, zinc and copper bromide in 1,2-dimethoxyethane by heating up to 70° C. to open the epoxy ring of said compound 3 with simultaneous removal of the chlorine atom to obtain 5-hydroxy-15β,16β-methylen-3β-pivaloyloxy-5βandrost-6-en-17-one 4:

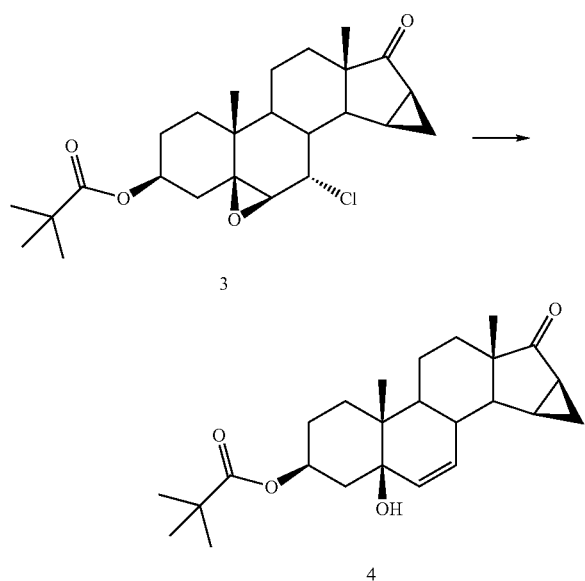

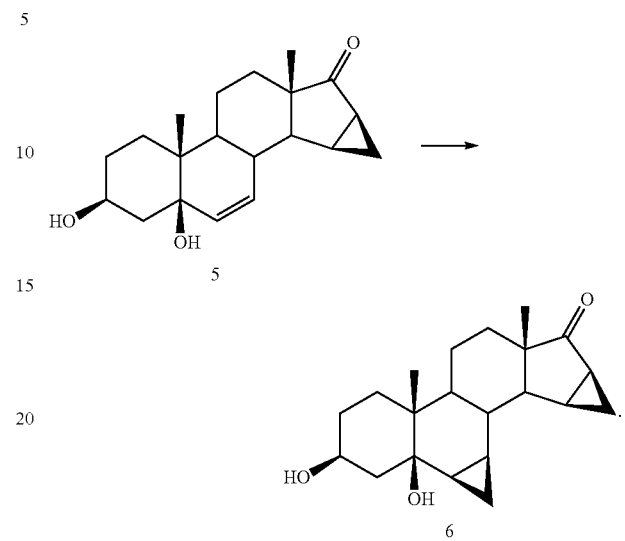

acetic acid and isopropanol to convert said compound 5 into 3β,5-dihydroxy-6β,7β,15β,16β-SSdimethylen-5β-androst-17-one 6:

d) removing the pivaloyl group in position 3 of compound 4 with potassium hydroxide in a tetrahydrofuran/methanol mixture in the presence of sodium perchlorate at room temperature, followed by addition of sulfuric acid to pH 7, to obtain 3β,5-dihydroxy-15β,16β-methylen-5β-androst-6-en-17-one 5:

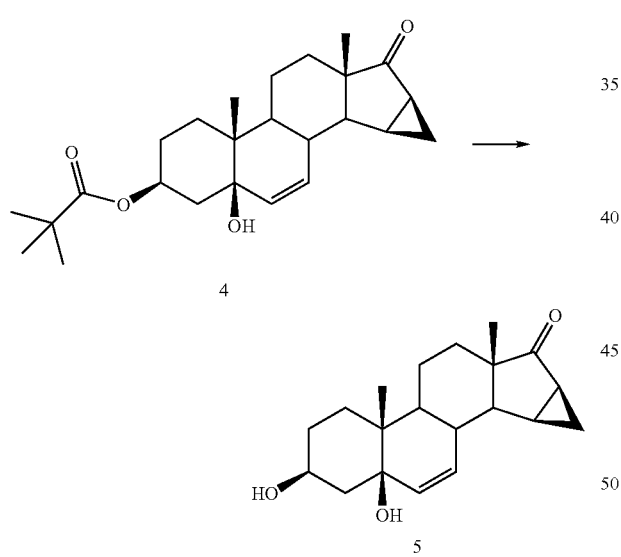

e) reacting said compound 5 with dibromomethane in 1,2-dimethoxyethane in the presence of zinc and copper bromide by heating up to 75° C. followed by addition of

14. A compound which is selected from the group consisting of:

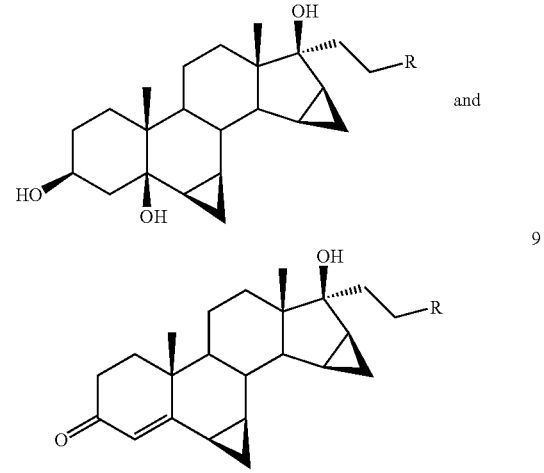

wherein in compound 8 R is as defined in claim 1 and in compound 9 R is —CH$_2$—OR$^I$— wherein R$^I$ is as defined in claim 1.

* * * * *